United States Patent [19]
Mathewson

[11] Patent Number: 6,142,965
[45] Date of Patent: Nov. 7, 2000

[54] VARIABLY ADJUSTABLE BI-DIRECTIONAL DEROTATION BRACING SYSTEM

[76] Inventor: Paul R. Mathewson, 7726 N. Buckboard Dr., Park City, Utah 84098

[21] Appl. No.: 09/004,010

[22] Filed: Jan. 7, 1998

Related U.S. Application Data

[60] Provisional application No. 60/039,104, Feb. 25, 1997.

[51] Int. Cl.$^7$ ..................................................... A61F 13/00
[52] U.S. Cl. ................................ 602/62; 602/23; 602/26; 602/60
[58] Field of Search ............................... 602/923, 26, 60, 602/62, 63; 2/455, 22; D24/190; 128/882

[56] References Cited

U.S. PATENT DOCUMENTS

| | | |
|---|---|---|
| 366,590 | 7/1887 | Lubin . |
| 967,585 | 8/1910 | Teufel . |
| 2,574,873 | 11/1951 | Jobst . |
| 2,646,796 | 7/1953 | Scholl . |
| 3,306,288 | 2/1967 | Rosenfield . |
| 3,307,546 | 3/1967 | Cherio et al. . |
| 3,419,003 | 12/1968 | Krauss et al. . |
| 3,504,672 | 4/1970 | Moon . |
| 3,529,601 | 9/1970 | Kirlkand . |
| 3,680,549 | 8/1972 | Lehneis et al. . |
| 3,724,457 | 4/1973 | Klatte . |
| 4,201,203 | 5/1980 | Applegate .................................. 602/26 |
| 4,269,181 | 5/1981 | Delannoy . |
| 4,425,912 | 1/1984 | Harper . |
| 4,503,846 | 3/1985 | Martin . |
| 4,697,583 | 10/1987 | Mason et al. . |
| 4,733,656 | 3/1988 | Marquette . |
| 4,802,466 | 2/1989 | Meyers et al. . |
| 4,941,462 | 7/1990 | Lindberg . |
| 4,986,264 | 1/1991 | Miller . |
| 5,018,514 | 5/1991 | Grood et al. . |
| 5,277,697 | 1/1994 | France et al. . |
| 5,277,698 | 1/1994 | Taylor . |
| 5,288,287 | 2/1994 | Castillo et al. . |
| 5,336,161 | 8/1994 | Lengyel . |
| 5,385,036 | 1/1995 | Spillane et al. . |
| 5,399,153 | 3/1995 | Caprio, Jr. et al. . |
| 5,407,421 | 4/1995 | Goldsmith . |
| 5,412,957 | 5/1995 | Bradberry et al. . |
| 5,433,699 | 7/1995 | Smith, III . |
| 5,437,619 | 8/1995 | Malewicz et al. . |
| 5,449,338 | 9/1995 | Trudell . |
| 5,460,599 | 10/1995 | Davis et al. . |
| 5,462,517 | 10/1995 | Mann . |
| 5,472,413 | 12/1995 | Detty . |
| 5,474,524 | 12/1995 | Carey . |
| 5,490,831 | 2/1996 | Myers et al. . |
| 5,512,039 | 4/1996 | White . |
| 5,520,622 | 5/1996 | Bastyr et al. . |
| 5,520,625 | 5/1996 | Malewicz . |
| 5,520,627 | 5/1996 | Malewicz . |
| 5,527,268 | 6/1996 | Gildersleeve et al. . |
| 5,873,848 | 2/1999 | Fulkerson .................................. 602/62 |

FOREIGN PATENT DOCUMENTS

| | | |
|---|---|---|
| WO 88/01855 | 3/1988 | WIPO . |
| WO 94/00082 | 1/1994 | WIPO . |

*Primary Examiner*—Kim M. Lee
*Attorney, Agent, or Firm*—Morriss, Bateman, O'Bryant & Compagni, P.C.

[57] ABSTRACT

A lightweight orthopedic brace having no rigid structural elements is constructed from flexible material and is designed primarily to provide for restriction of rotational movement and translation about the targeted joint by providing flexible bracing members which wind in a circumferentially spiraling manner about a target joint to provide active resistance to axial rotation and translation in the joint. The bracing members are adjustable to selectively increase the amount of resistance to axial rotation. The device may further comprise an undersleeve and/or an oversleeve to provide additional compression to the joint and to facilitate the circumferential winding of the bracing members. Construction of the orthopedic brace is such that resistance to rotation is achieved in both the internal and/or external directions. The orthopedic device has a multiplicity of uses, including, but not restricted to prophylactic, post-injury/surgery, as well as proprioceptive and retraining functions.

38 Claims, 13 Drawing Sheets

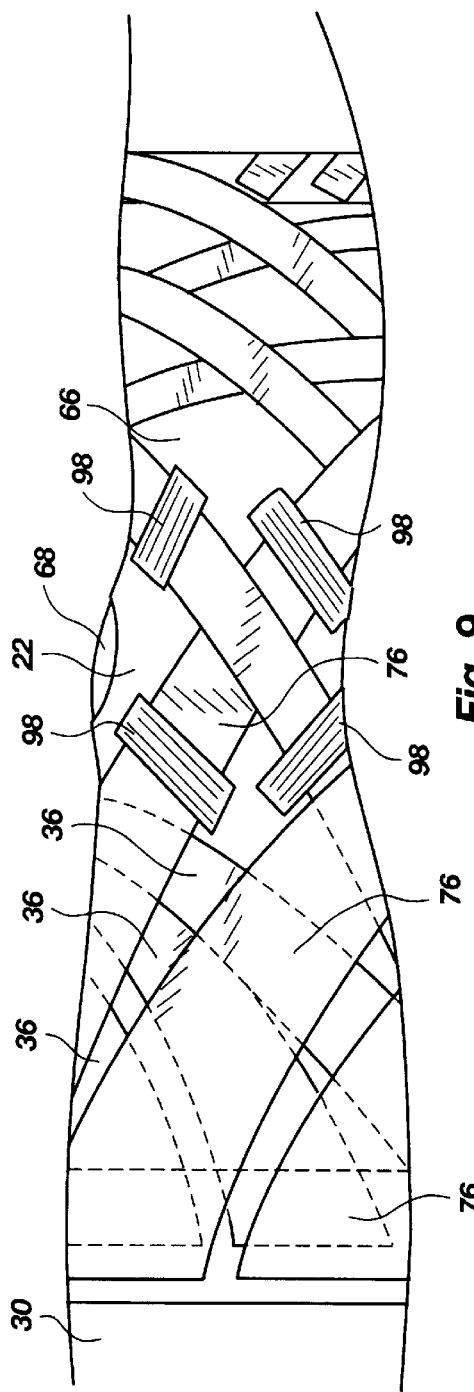
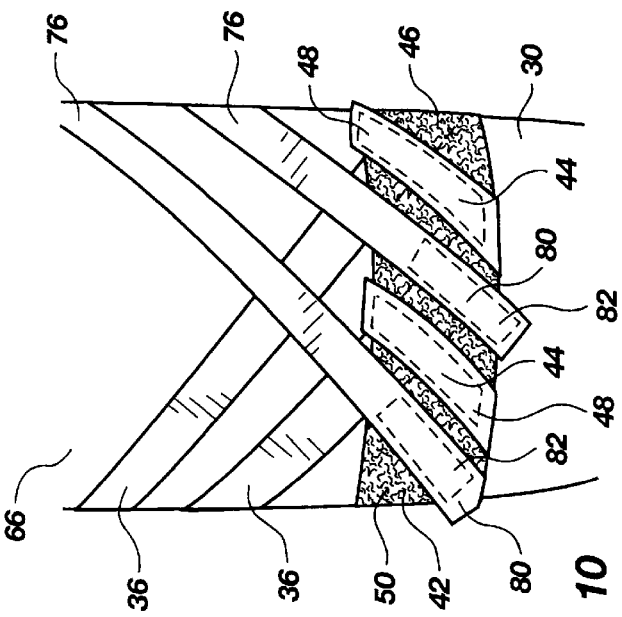
Fig. 9
Fig. 10

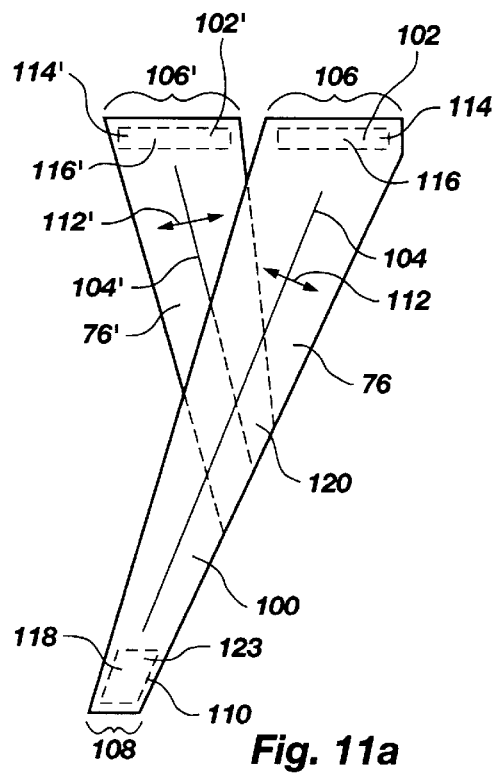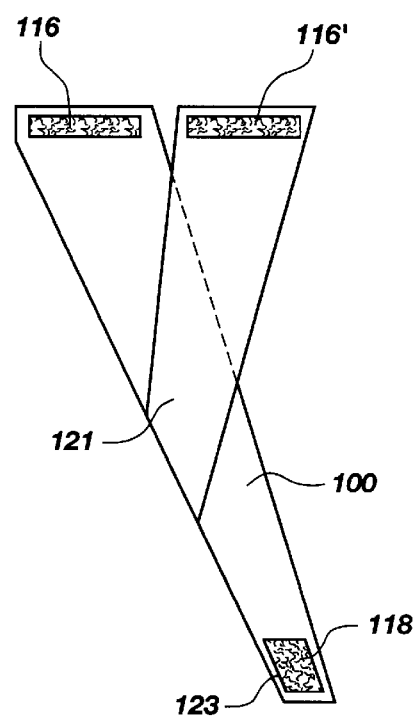
*Fig. 11a*  *Fig. 11b*
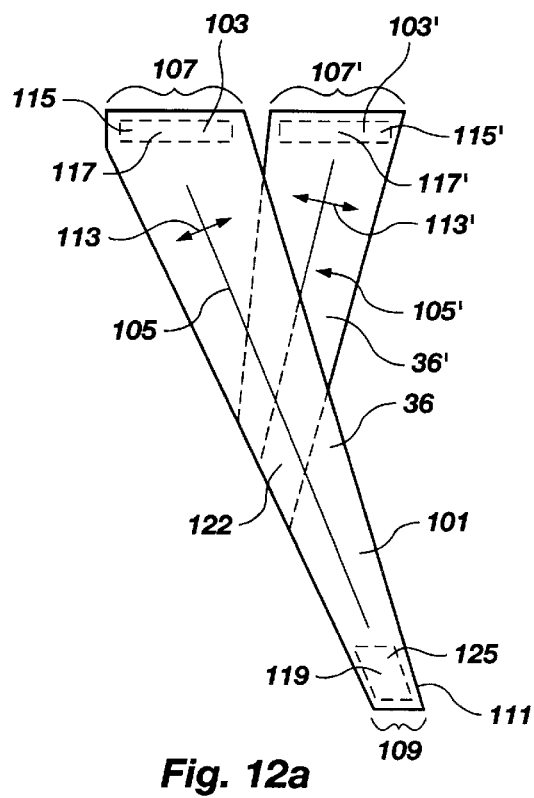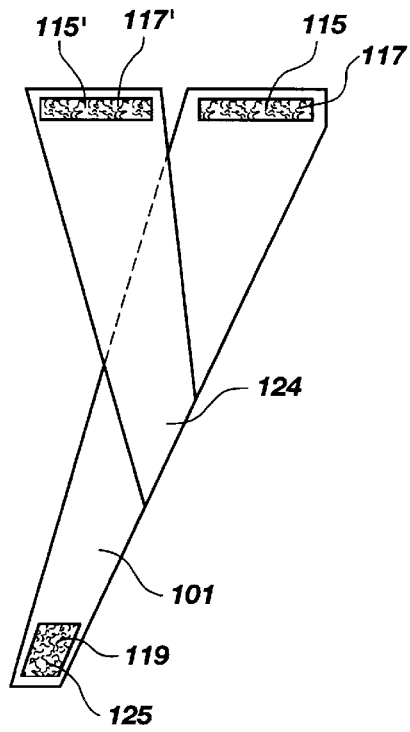
*Fig. 12a*  *Fig. 12b*

VARIABLY ADJUSTABLE BI-DIRECTIONAL DEROTATION BRACING SYSTEM

CROSS REFERENCE TO RELATED APPLICATION

This application claims the benefit of U.S. Provisional Application Ser. No. 60/039,104, filed Feb. 25, 1997.

BACKGROUND OF THE INVENTION

1. Field of the Invention

This invention relates generally to an orthopedic support device for physiological joints, and more specifically to an improved non-rigid orthopedic appliance and method for construction of a flexible orthopedic bracing system designed to limit both rotational and translational motion about the joints of human/animal limbs, especially around joints such as the knee.

2. Description of Related Art

Functional bracing of physiological joints, particularly the human knee joint, is a phenomenon of relatively recent origin. Substantial interest and effort in the bracing of knees in particular arose in the early 1970's, coincident with the origins of "sports medicine". Thus, orthotic bracing systems for various human joints are well known in the art and a wide variety of bracing systems have been developed to address a plethora of conditions for which bracing in some form has been thought to be therapeutically beneficial.

The bracing system in widest use over the last ten to fifteen years may be described as comprising a structural frame made up of a plurality of rigid support components which are linked in a dynamic fashion by one or more mechanical hinges. The frame is generally comprised of two sections, designed to attach to the soft tissue areas proximal and distal to the targeted joint, which are themselves joined by a mechanical hinge of varying design to allow the joint to move within the normal plane of motion. As used herein, "proximal" conventionally refers to a point situated toward the wearer's head while "distal" conventionally refers to a point situated away from the wearer's head. These devices may be described as hinge-post-band or hinge-post-shell devices depending on the configuration of the sections attaching to the soft tissue areas. In such examples, the orthotic can be described as a hard mechanical brace.

Hinged orthopedic bracing devices are commonly employed in an effort to provide stability to a skeletal joint which has been weakened by injury or other infirmity. Braces of this type have been designed primarily to help limit joint separation due to hyperextension or to varus or valgus deformation of the joint. Such devices, as applied to the knee joint, are represented by previously disclosed bracing systems in U.S. Pat. No. 4,503,846 to Martin, U.S. Pat. No. 4,697,583 to Mason et. al., U.S. Pat. No. 4,733,656 to Marquette, U.S. Pat. No. 4,802,466 to Meyers, U.S. Pat. No. 4,941,462 to Lindberg, U.S. Pat. No. 4,986,264 to Miller, U.S. Pat. No. 5,018,514 to Grood, et al., U.S. Pat. No. 5,277,697 to France, et al., U.S. Pat. No. 5,277,698 to Taylor, U.S. Pat. No. 5,336,161 to Lengyel, U.S. Pat. No. 5,433,699 to Smith, U.S. Pat. No. 5,460,599 to Davis, U.S. Pat. No. 5,490,831 to Myers, et al., and U.S. Pat. No. 5,527,268 to Gildersleeve, et al. All of these braces disclose bracing systems comprised of rigid structural elements linked by one or more mechanical hinges. Additional devices of similar construction, having structural elements connected by one or more mechanical hinges, have also been disclosed in U.S. Pat. No. 5,520,627 to Malewicz, as applied to the ankle, and in U.S. Pat. No. 5,437,619 to Malewicz, as applied to the elbow. A derotation brace for the wrist was also disclosed by Malewicz in U.S. Pat. No. 5,520,625.

The brace disclosed by Gildersleeve et al., a current example of the series of braces representing this technology, comprises a hinged orthopedic brace having a frame and one or more pads attached thereto that provide support for the brace when the frame is mounted on the body. This frame is a rigid structure, made up of two sections, one above and one below the joint, dynamically linked together by two hinges on either side of the knee. The frame is mounted onto the body of a user in such a manner that the hinges are positioned to traverse the joint being stabilized. The support frame is attached to the body using a system of pliant bands. This bracing device, like all similarly constructed rigid braces with mechanical hinges, is designed to stabilize the joint by restricting movement to one plane corresponding, in the case of a knee, to normal flexion and extension. Using the knee as the primary example, devices utilizing this current bracing technology are designed to fit around the affected joint in a manner which attempts to limit both hyperextension and lateral movement of the joint. This lateral movement might result from a force applied to the region at or near the lateral or medial condyle aspects of the knee joint, approximately perpendicular to the normal flexion/extension plane of motion in this joint.

Many braces, constructed in the aforementioned manner, have also claimed to attenuate rotational deformations of the knee in addition to lateral and hyperextensive displacements. Among such disclosures are U.S. Pat. No. 4,503,846; U.S. Pat. No. 4,733,656; U.S. Pat. No. 4,802,466; U.S. Pat. No. 4,986,264 and U.S. Pat. No. 5,018,514. All of the aforementioned references which disclose braces claiming to provide such rotational stability are of the hinge-post-band/shell construction. In all such bracing systems, any rotational stability that may be provided is linked to both the medial-lateral and the anterior-posterior stability afforded by the brace. However, rotational stability is not the primary design feature of these braces, but a presumed consequence stemming from that medial-lateral and anterior-posterior stability which the bracing system may provide. Any such stability depends on the ability of the brace to remain stationary with respect to the body after application of the brace and during its use.

In all such rigid, hinged bracing systems, the stability of the brace on the leg is provided by pliant straps which encircle the leg at specific locations. The straps require considerable tightening about the leg to assure that the relatively heavy and rigid devices stay in place about the knee or leg. Even so, the weight of such devices results in the device migrating downwardly on the leg and any rotational stability that might be provided by such devices is lost. In theory, post-hinge-band/shell-type bracing systems claiming to restrict lateral, rotational and/or hyperextensive movement should be of some value in terms of ameliorating the incidence of joint injuries, but that has not been demonstrated biomechanically. The design of these braces is directed to reducing the likelihood of re-injury resulting primarily from medial/lateral and hyperextensive forces rather than those resulting from rotational forces.

While a significant number of injuries occur as a result of lateral and hyperextensive forces on the knee (as well as other joints), it is recognized that a great many joint injuries, especially those involving the anterior cruciate ligament (ACL) of the knee, result from a torsional rotation force about the joint. Current mechanical hinged braces have, as yet, not demonstrated biomechanical efficacy in helping to prevent injuries resulting from such rotational forces.

Other bracing systems have also been disclosed which are less rigid and/or mechanical, such as that disclosed in U.S. Pat. No. 3,680,549 to Lehneis. Still other bracing systems are disclosed which employ soft materials in an effort to provide some support to a joint. Such devices do not, and are not specifically meant to, limit the movement of a joint under stress and, therefore, are not able to fulfill the role of an orthopedic brace. Such devices are disclosed in U.S. Pat. No. 5,399,153 to Caprio, et al., in U.S. Pat. No. 5,407,421 to Goldsmith, in U.S. Pat. No. 5,462,517 to Mann, in U.S. Pat. No. 5,472,413 to Detty and in U.S. Pat. No. 5,474,524 to Carey, among others. Fabric bandages have also been used as joint supports, as disclosed in U.S. Pat. No. 366,590 to Lubin, U.S. Pat. No. 967,585 to Teufel and U.S. Pat. No. 5,385,036 to Spillane, et al. Those devices are stretchably elastic in all directions and thus are designed only to provide a constant, non-variable level of compression about the affected body area. These devices are not designed to limit joint rotation. Indeed, elastic fabric bandages are not effective at preventing joint rotation under physiologically significant loads because of their elasticity in all dimensions. Thus, they cannot accomplish the objectives for which a true bracing system is designed.

Known bracing systems are not specifically designed to effectively constrain axial rotation about a human or animal joint. Thus, it would be advantageous in the art to provide an orthotic device which is specifically designed to provide substantial restriction of axial rotation, as well as translation, about a physiological joint. Further, it would be advantageous to provide such an axial derotation orthotic with the characteristics of being lightweight and flexible, having no rigid structural components or hinged mechanisms, and providing for comfortable, sustained protection while the wearer engages in normal activity.

BRIEF SUMMARY OF THE INVENTION

In accordance with the present invention, a bracing apparatus is structured to delimit axial rotation of an articulating joint by providing a substantially non-rigid, circumferentially spiraling member which exerts resistance to rotation about the longitudinal axis of the joint, thereby delimiting axial rotation of the joint while enabling normal flexion and extension through the joint. The present invention may be used in humans and animals alike, and may be adapted for use with virtually any articulating joint which may require the limitation of axial rotation therethrough. However, for simplification of description, the invention is described herein with respect to a human knee joint as merely one exemplar application of the invention.

The present invention is comprised of a substantially non-rigid member which extends over and about the target joint and extends from a location proximal to the joint to a position distal to the joint along the longitudinal axis of the joint. The substantially non-rigid member is constructed to provide resistance to rotation about the longitudinal axis of the joint by providing circumferentially spiraling means capable of delimiting rotation about the joint while allowing normal flexion and extension of the joint (i.e., rotation through a lateral axis which is perpendicular to the longitudinal axis of the joint).

In one exemplar embodiment of the present invention, the bracing apparatus is comprised of at least one circumferentially and spirally windable elongated bracing member, a first bracing member support and a second bracing member support. The elongated bracing member is of sufficient length to allow the bracing member to be wound in a circumferentially spiraling manner about the joint and to extend from a location above the joint to a location below the joint. Bracing members of this invention are substantially non-rigid and are flexible so that they may be wound about the area of the joint. The bracing members, however, are preferably substantially inelastic along a longitudinal axis, or from one end of the bracing member to the other end of the bracing member. The bracing members may, most suitably, be elastic in a direction normal to the longitudinal axis thereof to accommodate changes in muscle mass distribution during muscle contraction. Alternatively, the bracing members may be inelastic in a direction normal to the longitudinal axis thereof.

In one presently preferred embodiment, the bracing members of the invention may be elongated bands of material which are sized in length to be circumferentially and spirally wound about the limb, above and below the joint. Suitable materials which may be used in construction of the elongated bands include woven fabrics, nonwoven natural or artificial materials, and particularly those which provide elasticity only in a direction normal to the longitudinal axis thereof.

A first bracing member support is positioned to one side of the joint and the second bracing member support is positioned to the other side of the joint. For example, the first bracing member support may be positioned about the thigh in a location proximal to (i.e. above) the knee joint and the second bracing member support may be positioned about the calf distal to (i.e. below) the knee joint. The first and second bracing member supports provide a means for attaching the circumferentially spiraling bracing members thereto and are constructed to allow variably adjustable securement of the bracing members thereto to enhance delimited rotation about the joint. In a presently preferred embodiment, the first and second bracing member supports are continuous collars which are sized to extend about an area of the body (e.g., a limb or digit) in proximity to the joint. The collars are further structured to provide a means for releasably attaching the bracing members thereto to readily provide adjustability of the bracing members. Any structure which suitably provides a stable point for adjustably anchoring the bracing members thereto may be employed as bracing member supports.

The present invention may also include at least one flexible sleeve which is sized to be positioned against the body and about which the circumferentially windable bracing members are positioned. In a preferred embodiment, the first and second bracing member supports, or collars, are integrally attached to, or are formed with, the flexible sleeve. A second flexible sleeve may be employed to extend over the bracing members once they are wound about the joint, and may be sized to be essentially co-extensive with the first flexible sleeve. The second flexible sleeve may operate to hold the bracing system in place on the limb and may provide a uniform compressive support system at the same time.

The derotation bracing apparatus of the present invention may be formed on the wearer's body by circumferentially and spirally winding at least one bracing member about the body on either side of the joint. More specifically, the first bracing member support may be positioned to one side of the joint (e.g., placed about the thigh and above the knee), the second bracing member support may be positioned on the other side of the joint (e.g., placed about the calf and below the knee), and the bracing member or bracing members may be initially secured at one end thereof to a bracing member support. The bracing member or members are then circumferentially wound, in a spiraling fashion, about the body (e.g., the leg) and are secured to the other bracing member support. At least one or a plurality of bracing members may be circumferentially and spirally wound about the body in the same direction. In a particularly preferred embodiment, however, a first plurality of bracing members are circumferentially and spirally wound about the body in one direction (e.g., levorotatory) and a second plurality of bracing members are circumferentially and spirally wound in the opposite direction (e.g., dextrorotatory) about the body to provide restriction to rotation about the joint in both internal and external directions. As used herein, the direction of turn of "levorotatory" and "dextrorotatory" is determined by the longitudinal axis formed through the target joint and by initiation of turning from the proximal end of the bracing apparatus.

One may envision this restrictive action to rotation about the joint by visualizing the ends of each bracing member as two points, one point fixedly positioned on the surface of the limb above the joint and the other point fixedly positioned on the surface of the limb below the joint. At any given angle of flexion of the joint, the distance between these two points is fixed as long as the joint remains in the single plane defined by "normal" flexion/extension. For example, a bracing member of substantially fixed or inelastic length which is wrapped in a circumferentially spiraling orientation around the limb and fully extended in length when the limb is in a normal (i.e. relaxed frontal) orientation, defines a certain distance between the two fixed points on the limb and also defines a certain circumference about the limb in that orientation. As rotational force is applied to the joint (e.g., the femur rotates axially relative to the tibia), the fixed points either proximal or distal to the joint move out of the defined single plane of motion and the distance between the two fixed points is increased. The only way that such an increase in the distance between the two fixed points can be accommodated by a substantially non-elastic bracing member of the present invention is through a decrease in the circumference defined by the circumferentially spiraling bracing member about the limb. The dynamic decrease in circumference of the bracing member as axial rotation proceeds results in compression on the muscle tissue of the limb and generates an active restraining force, thereby delimiting or actively resisting further axial rotation. Thus, for example, each bracing member wound about the limb in one given direction will exert compressive restraining force as axial rotation occurs in the direction opposite the winding direction of the bracing members. The present brace has the ability to respond to rotation about the joint by gradually and dynamically increasing compressive resistance as the degree of rotation about the joint increases as well as gradually and dynamically reducing the compressive force as the degree of rotation decreases with a return to a normal, unrotated position. The brace is actively responding to rotation at all times.

Circumferentially- and spirally-binding the body on either side of the joint as described provides active resistance to axial rotation of the joint, as well as resistance to anterior tibial translation (i.e., anterior movement of the head of the tibia relative to the intercondylar surface of the femur), because of the substantially longitudinal inflexibility of the circumferentially-wound bracing member. The active resistance provided by the present derotation bracing apparatus may be selectively increased by detaching one end of a bracing member from the bracing member support, rotating the segment of the body engaged by the apparatus (e.g., the leg) and then re-securing the bracing member to the bracing member support. When the body segment (e.g., the leg) is brought back to its normal position following rotation, the adjusted bracing member will tighten even more about the body to provide increased active resistance to axial rotation. This designed adjustability allows not only for selectively adjusting the functional resistance to rotation, but also provides for the accommodation of different limb dimensions among the normal population. Thus, the design provides a means for adjusting the tension in each of the bracing members, which affects the degree to which axial rotation about the joint is resisted.

The positioning of the bracing members about the body may be aided by means of additional fabric loops attached to the flexible sleeve when employed. The loop fabric is itself elastic and is applied to the flexible sleeve in a manner which does not effect the elastomeric characteristics of the sleeve. In a present embodiment, the bracing members are wrapped in both a clockwise (dextrorotatory) and counter-clockwise (levorotatory) direction about the body (e.g., the leg) in order to provide active resistance to rotation about the joint in the case of either internal or external tibial rotation. Internal tibial rotation may be described, for example, as rotating the body to the left while standing on the stationary left foot. However, depending on the specific functional imperative, the bracing members may be applied to circumferentially spiral in one direction only to address specific rotation-resistance requirements.

The present invention is directed to providing a new form of orthopedic brace which more effectively controls or delimits axial rotation in a physiological joint. Unlike prior examples of orthopedic braces, the present device is a flexible arrangement of bracing members which actively resist axial rotation in the joint by providing a flexible, circumferentially spiraling bracing device. A further consequence of this restrictive action is that translation in the joint is also delimited. The present invention effectively eliminates the rigid structural elements, as well as the mechanical hinge structures of previous orthopedic bracing systems, rendering it easy to use, comfortable to wear and suitable for use during normal everyday activity, including sporting activities. These and other advantages of the present invention are more fully described in the description of the illustrated embodiments.

BRIEF DESCRIPTION OF THE SEVERAL VIEWS OF THE DRAWINGS

In the drawings, which illustrate what is currently considered to be the best mode for carrying out the invention:

FIG. 9 is a side view of the human leg illustrating the positioning of the bracing members as well as means used to guide the positioning of the bracing members;

FIG. 10 is a front view of the lower portion of a human leg illustrating a manner of releasably attaching the bracing members which wind about the leg in both the dextro- and levorotatory direction;

FIG. 11(a) is a plan view showing the outer facing surface of an alternative embodiment of the bracing member which may be wound about the leg in a dextrorotatory direction;

FIG. 11(b) is a plan view showing the inner facing surface of the alternative embodiment of the bracing member shown in FIG. 11(a) which may be wound about the leg in a dextrorotatory direction;

FIG. 12(a) is a plan view showing the outer facing surface of an alternative embodiment of a single bracing member which may be wound about the leg in a levorotatory direction;

FIG. 12(b) is a plan view showing the inner facing surface of the alternative embodiment of the single bracing member shown in FIG. 12(a) which may be wound about the leg in a levorotatory direction;

DETAILED DESCRIPTION OF THE INVENTION

Figure 1:
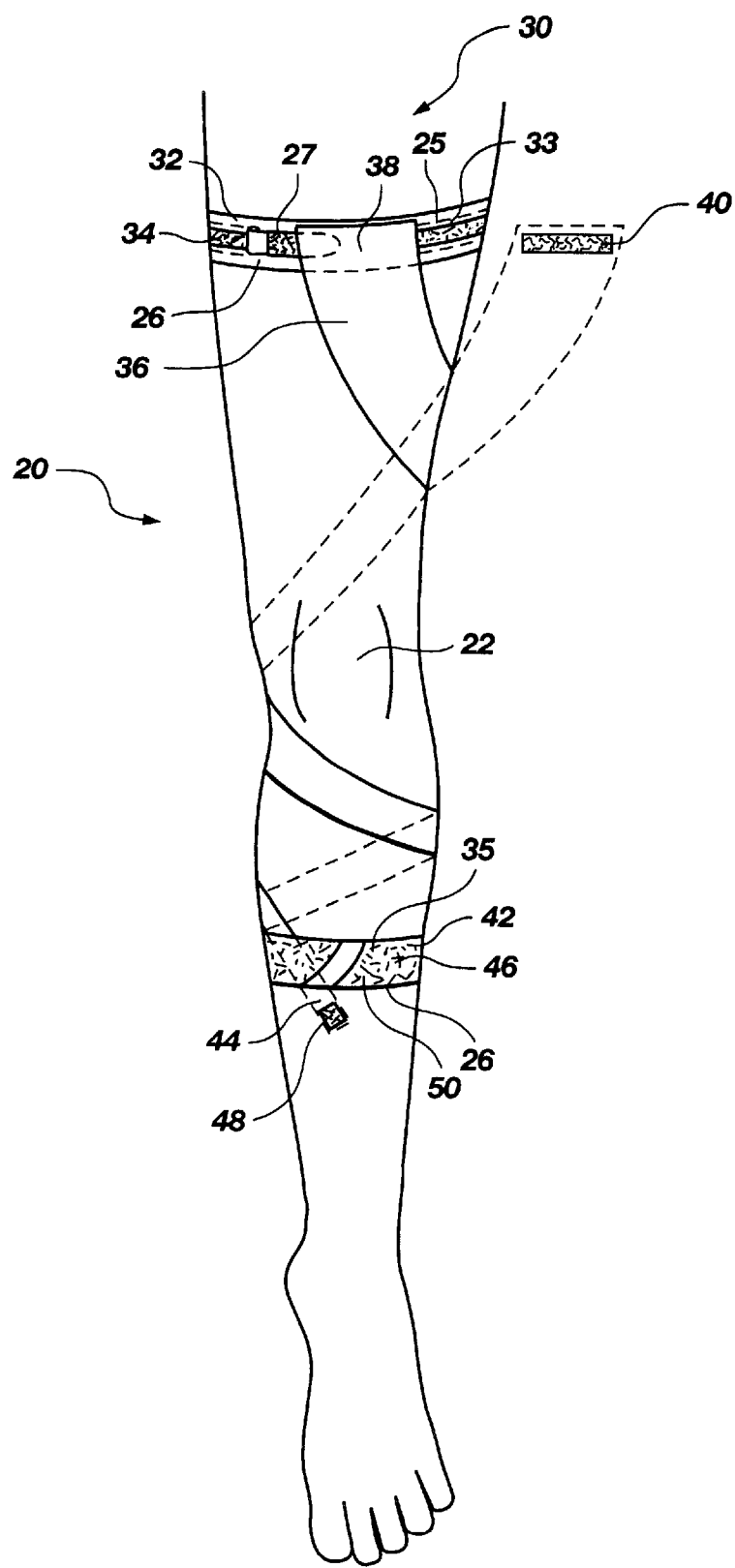
FIG. 1 is a front view of a human leg illustrating the essential elements of the present invention in place on the human leg, certain details being shown in partial phantom.

The principal elements of the present invention are illustrated in FIG. 1 which shows, by way of example only, the use of the invention in connection with delimiting axial rotation in the human knee joint. The present invention, generally at 20, comprises a first bracing member support 32 for positioning about the leg 30, a second bracing member support 42 for positioning about the leg 30, and at least one circumferentially and spirally-wound bracing member 36 sized in length to extend between the first bracing member support 32 and the second bracing member support 42. Both the first bracing member support 32 and the second bracing member support 42 may generally be configured as a collar which is sized to encircle the leg 30 at a given distance above the knee joint 22 and to encircle the leg 30 at a given distance below the knee joint 22, respectively. The collar 26 may suitably be formed with an amount of adjustability or elasticity which allows the collar 26 to be adapted to legs of various circumferential dimension, and which allows the collar 26 to expand and contract readily with muscle movement. The collar 26 may be made of a single strip of material having free ends which may be joined together about the leg. Alternatively, the collar 26 may be made of a continuous band of material having a selected elasticity.

Both the first bracing member support 32 and the second bracing member support 42 may be constructed to releasably support one or more bracing members 36 in position about the leg 30. By way of example, the single-width first bracing member support 32, as shown in FIG. 1, may be constructed with a securement means, for example, a continuous band of hook and loop material 34 to which the proximal end 38 of the bracing member 36 may be attached by a corresponding securement means, here, for example, a hook and loop tab 40 located at the proximal end 38 of the bracing member 36, shown in partial phantom in FIG. 1. The distal end 44 of the bracing member 36 may be releasably supported by the second bracing member support 42 in a similar arrangement of securement means, for example, hook and loop material 46 associated with the second bracing member support 42 engaging a corresponding hook and loop tab 48 positioned at the distal end 44 of the bracing member 36. Alternatively, the hook and loop securement means on the bracing member supports 32 and 42 may be individual, discrete tabs of hook and loop material attached to the outward facing surface 33 and 35, respectively, of the bracing member supports 32 and 42. The distal end 44 of the bracing member 36 may also be fixedly secured to the second bracing member support 42.

A strap 25 (shown in partial phantom), which is sized to encircle the limb, may be integrated into the first bracing member support 32 to provide an additional means of tightening, or circumferentially adjusting, and securing the first bracing member support 32 in place about the leg 30. The strap 25 has an exposed end 27 (shown in partial phantom) which is graspable for pulling and tightening the strap 25. End 27 may be fabricated with a suitable attachment means, such as, for example, a hook and loop material positioned on both the inner facing and outer facing surfaces of the end 27 to properly engage the hook and loop material 34 of the first bracing member support 32, as well as to engage the hook and loop material 40 positioned at the proximal end 38 of the bracing member 36. A similar strap may be incorporated into the second bracing member support 42.

Figure 2:
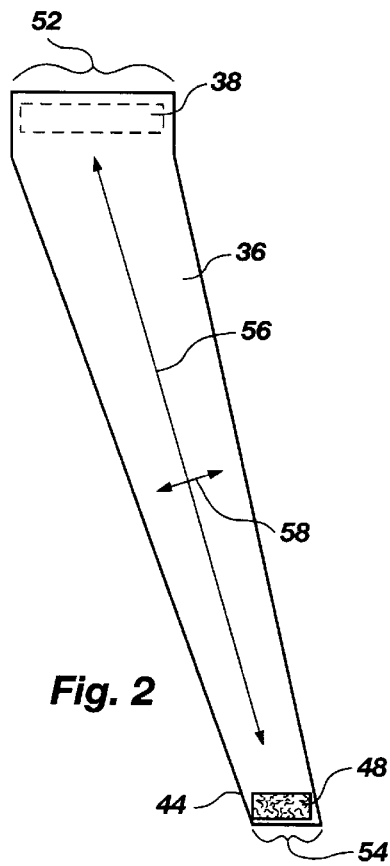
FIG. 2 is a plan view of a first embodiment of a single bracing member which may be wound about the leg in a levorotatory direction, the outer facing surface being shown.
Figure 3:
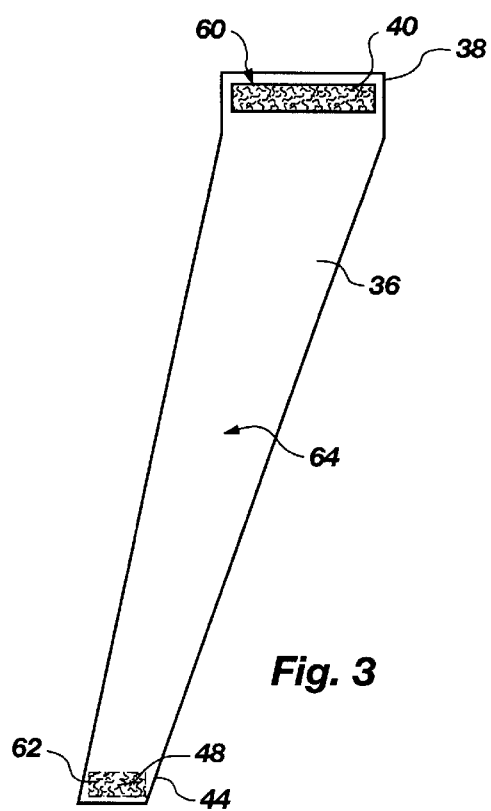
FIG. 3 is a plan view of the single bracing member shown in FIG. 2, but illustrating the inner surface of the member.

As illustrated more fully in FIGS. 2 and 3, the bracing member 36 comprises a length of material which has a longitudinal axis 56 formed through the length thereof. As illustrated, the bracing member 36 may preferably be constructed to have a greater width 52 at the proximal end 38 compared with the width 54 at the distal end 44. As such, the bracing member 36 may be considered to have a tapered configuration. The material from which the bracing member 36 is made may be any suitable material which provides a certain flexibility to permit winding the brace member 36 about the leg 30 in a circumferentially spiraling fashion as illustrated in FIG. 1. It is important, however, in the delimitation of the axial rotation about the knee joint 22 that the bracing member 36 be substantially inelastic or non-extendible along the longitudinal axis 56 thereof. The material of the bracing member 36 may also be substantially inelastic in a direction 58 normal to the longitudinal axis 56 of the bracing member 36. However, some elasticity in direction 58, normal to the longitudinal axis 56 of the bracing member 36, may be beneficial in providing expandability of bracing member 36 in response to muscle contraction to accommodate changes in muscle configuration as the muscles expand and contract with movement.

As shown in FIG. 3, the bracing member 36 may be constructed with a securement structure 60 at the proximal end 38 thereof for releasable securement of the bracing member 36 to the first bracing member support 32. The securement structure 60 may be, for example, a hook and loop tab 40 or any other suitable device. The distal end 44 of the bracing member 36 may also be constructed with a securement structure 62 which may be, for example, a hook and loop tab 48. To enable attachment of the bracing member 36 to the second bracing member support 42, the distal end 44 of the bracing member 36 may be passed behind the second bracing member support 42 (i.e. between the second bracing member support 42 and the leg 30) as shown in FIG. 1 and may then be inverted back over the second bracing member support 42 to engage the corresponding hook and loop material 46 on the second bracing member support 42 with the hook and loop tab 48 of the bracing member 36. Thus, the securement structure 62 at the distal end 44 of the bracing member 36 may be positioned on the outer facing surface of the bracing member support 42 as shown in FIG. 2. Alternatively, as shown in FIG. 3, the inner surface 64 (i.e. that surface which is positioned against the wearer's body) of the bracing member 36 may be constructed with a hook and loop tab 48 (shown in phantom) at the distal end 44 thereof to enable attachment of the bracing member 36 to the outer facing surface 50 (FIG. 1) of the second bracing member support 42.

The embodiment of the invention shown in FIG. 1 is the simplest configuration in that only one bracing member 36 is shown circumferentially and spirally positioned about the leg 30. Although the use of a single bracing member 36 will provide some delimitation of axial rotation about the knee joint 22, additional bracing members 36 wound about the leg 30 will maximize the active resistance to rotation. Thus, in an alternate embodiment shown in FIG. 4, a plurality of bracing members 36 may be circumferentially wound about the leg in a spiraling fashion. Each bracing member 36 is releasably secured to, and extends between, the first bracing member support 32 and the second bracing member support 42 as previously described.

Figure 4:
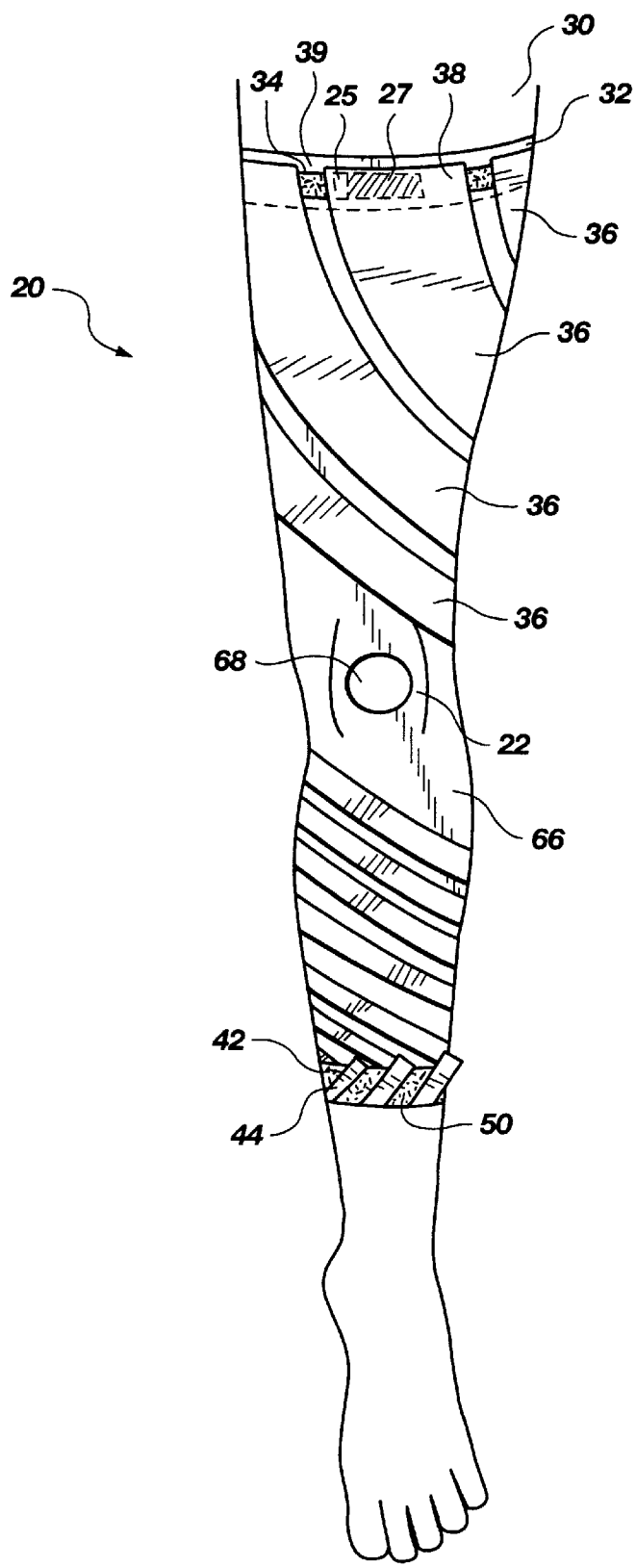
FIG. 4 is a front view of a human leg illustrating the positioning of a plurality of bracing members wound about the leg in a single direction.

Further, as illustrated in FIG. 4, the present invention 20 may include a flexible undersleeve 66 which is positionable over the skin of the leg 30 and is sized in length to extend from a distance above the knee joint 22 to a distance below the knee joint 22. In this embodiment, the first bracing member support 32 and the second bracing member support 42 may be attached to or integrally formed with the flexible undersleeve 66. Additionally, flexible undersleeve 66 may be further modified to prevent slippage of the flexible undersleeve 66 against the leg 30 by use of a flexible adjustable strap 25 positioned between the undersleeve 66 and the first bracing member support 32 to provide additional adjustable tightness around the thigh. The flexible undersleeve 66 may also, or alternatively, be modified by contacting the inner surface of the undersleeve 66 with a material or substance which imparts an increased coefficient of friction between the flexible undersleeve 66 and the leg 30, such as a rubberized material. Alternatively, the undersleeve 66 may be constructed from a material having a sufficiently high coefficient of friction to prevent slippage of the undersleeve 66, and thus the bracing member supports 32, 42 against the skin. It may also be advantageous to allow for a patellar relief space 68 by providing a cut-out in the flexible undersleeve 66 directly over the patellar region of the knee joint 22.

It is inherent in the design of the present invention that one or a plurality of bracing members 36 wound, as described, in a circumferentially spiraling fashion about the leg 30, in the same direction, whether levorotatory or dextrorotatory, will provide active resistance to axial rotation about the knee joint 22 in one direction only. While this may be a desirable construction in some cases, it may be advantageous to provide rotational stability in both the internal and external directions of axial rotation in a single device. Thus, a further alternative embodiment illustrated in FIG. 5 shows the addition of a bracing member 76 wound in the opposite direction (here dextrorotatory) to the bracing members 36 illustrated in FIG. 4, thereby providing additional delimitation of axial rotation in a direction opposite to that provided by bracing members 36.

Figure 5:
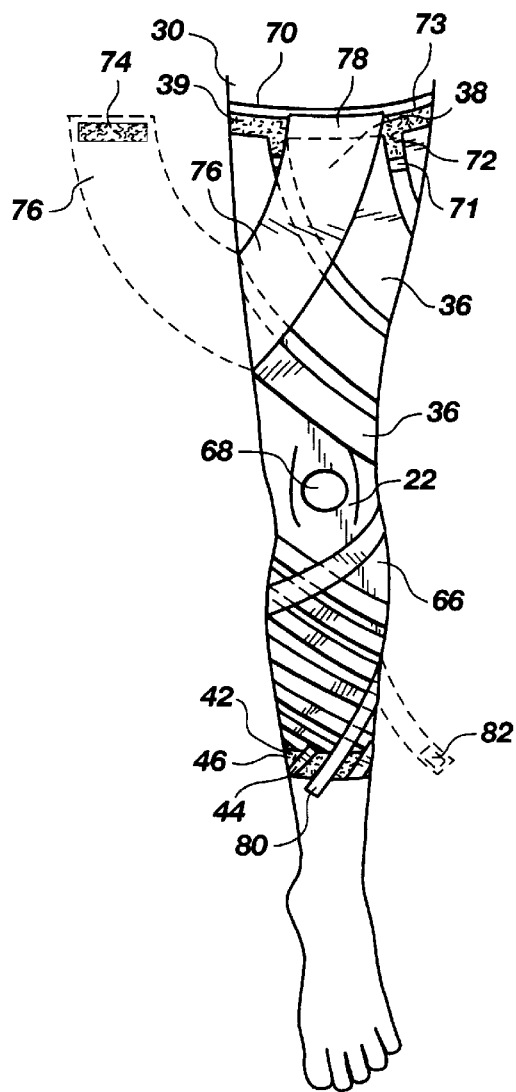
FIG. 5 is a front view of the leg shown in FIG. 4 with an additional single bracing member wound about the leg in the opposite direction.

In the embodiment shown in FIG. 5, a double-width first bracing member support 70 may be used instead of bracing member support 32. Double-width first bracing member support 70 is of sufficient width to accommodate the securement thereto of the proximal ends 38 and 78 of bracing members 36 and 76, respectively, wound in a circumferentially spiraling fashion about the leg 30 in both dextro- and levorotatory directions. The width of double-width first bracing member support 70 may be provided by using two separate bracing member support collars adjacently positioned or, alternatively, by making one bracing member support with sufficient width to accommodate the attachment of bracing members 36 and 76 wound in opposing directions. Thus, in the illustrated embodiment, both bracing member supports 42 and 70 may be constructed to releasably support one or more bracing members 36 and 76 in position about the leg 30.

As previously described for bracing member support 32, double-width first bracing member support 70 may be constructed with a releasable securement means, for example, a continuous band of hook and loop material 72 attached thereto to which the proximal end 78 of bracing member 76 may be attached by a corresponding hook and loop tab 74, as shown in partial phantom in FIG. 5, or other suitable means. Alternatively, the securement means on the double-width first bracing member support 70 may also be, for example, individual, discrete tabs of hook and loop material attached to the outward facing surface 39 of the double-width first bracing member support 70.

The proximal end 38 of each bracing member 36 is releasably attached to the double-width bracing member support 70 as previously described with respect to attachment to bracing member support 32 and is positioned at the distal portion 71 of the double-width bracing member support 70. The proximal ends 78 of the bracing members 76 are attached to continuous hook and loop material 72 attached to the proximal portion 73 of double-width first bracing member support 70 by engagement of corresponding hook and loop material 74 attached to the proximal ends 78 of the bracing members 76. The distal end 80 of the bracing members 76 may be releasably attached to the second bracing member support 42 by a corresponding arrangement of, by way of example, hook and loop material 46 and tabs 82 (shown in phantom) positioned at the distal end 80 of bracing member 76.

The embodiment shown in FIG. 5 represents a simplified configuration in which only one bracing member 76 is shown wound in a circumferential spiraling fashion in a direction opposite to that shown for bracing members 36. This configuration would provide some active resistance to axial rotation about the knee joint 22 in the direction opposite to that provided by bracing members 36. However, as described for bracing members 36, additional bracing members 76 wound about leg 30 will maximize active resistance to axial rotation about the knee joint 22, in the direction opposite to the resistance to axial rotation provided by bracing members 36, thus maximally stabilizing the knee joint 22 in both directions with respect to axial rotation.

Figure 6:
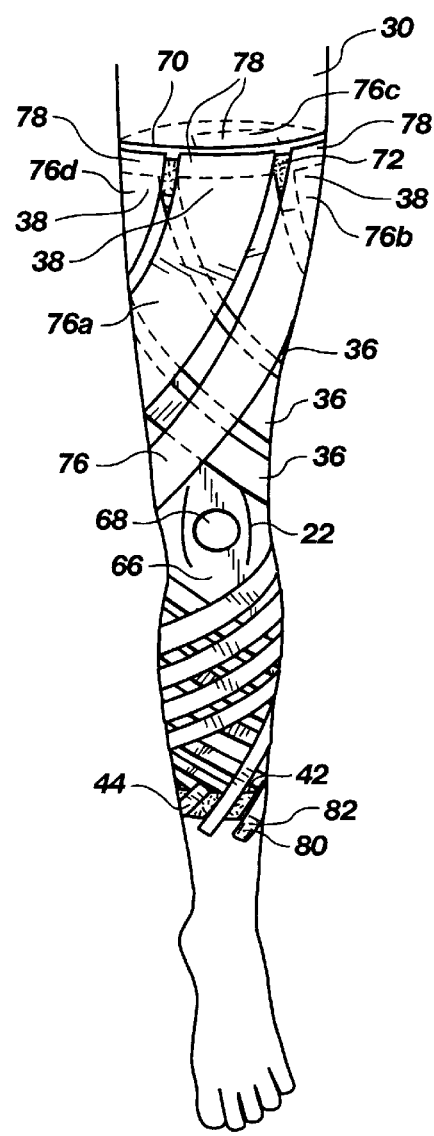
FIG. 6 is a front view of the leg shown in FIG. 5 illustrating a plurality of additional bracing members wound about the leg in both directions.

A preferred embodiment illustrating an arrangement in which a plurality of bracing members 36 and 76 are wound in opposite circumferential spiraling fashion about the knee joint 22 of the leg 30 is shown in FIG. 6. By way of example only, this embodiment illustrates the positions of four bracing members 36 wound in a levorotatory direction down the leg 30 and around the knee joint 22 and four bracing members 76 wound in a dextrorotatory direction down the leg 30 and around the knee joint 22. The winding of bracing members 36 and 76 may be accomplished in any of several configurations. In a preferred configuration illustrated in FIG. 6, no bracing members are located directly over the patellar surface or in the area directly posterior to the knee joint 22.

The proximal ends 38, 78 of each bracing member 36 or 76, respectively, may be releasably secured to the double-width first bracing member support 70 at positions oriented approximately posterior, anterior, medial and lateral to the leg 30. The posterior and anterior attached bracing members, 76c and 76a, respectively, each describe approximately three-quarters of a turn above the knee joint 22 and approximately one turn below the knee joint 22, attaching at their distal ends 80 to the second bracing member support 42 by means of, for example, a hook and loop tab 82 (in phantom). The lateral and medial attached bracing members, 76b and 76d, respectively, describe approximately one-half turn above the knee joint 22 and approximately one turn below the knee joint 22, attaching to the second bracing member support 42 by means of a suitable securement structure, shown here as a hook and loop tab 82 (shown in phantom). The bracing members 36, though shown only in phantom in FIG. 6, attach to the bracing member supports 70 and 42, and wind in the same manner as previously described.

Although the figures herein show the circumferentially spiraling bracing members 36 and 76 as winding with approximately one-half and three-quarters of a turn above the knee joint 22 and approximately one turn below the knee joint 22, it is not intended that this particular configuration be construed as the only configuration possible. In fact, a wide range of such winding configurations may be employed to accomplish the intended functionality of the present invention.

The embodiment illustrated in FIG. 6 shows that the bracing members 76 circumferentially encircle the leg 30 and pass the knee joint 22 at either the lateral or medial condyle portion of the knee joint 22. In this arrangement, the patellar region of knee joint 22 as well as the area posterior to knee joint 22 are not covered by bracing members 36 or 76 as they wind around the leg 30, thereby leaving the knee joint 22 unencumbered for normal flexion and extension. Alternatively, the bracing members can be positioned to wind in a circumferential spiraling fashion in which one or more of the bracing members may cross on or near the patellar region and/or the region posterior to the knee joint 22.

Figure 7:
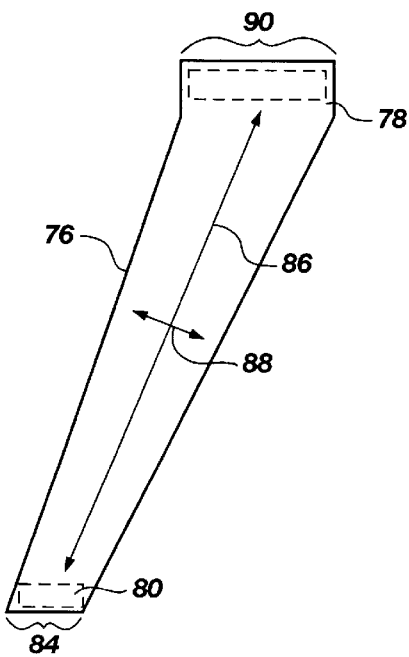
FIG. 7 is a plan view of a first embodiment of a single bracing member which may be wound about the leg in a dextrorotatory direction, the outer facing surface being shown.
Figure 8:
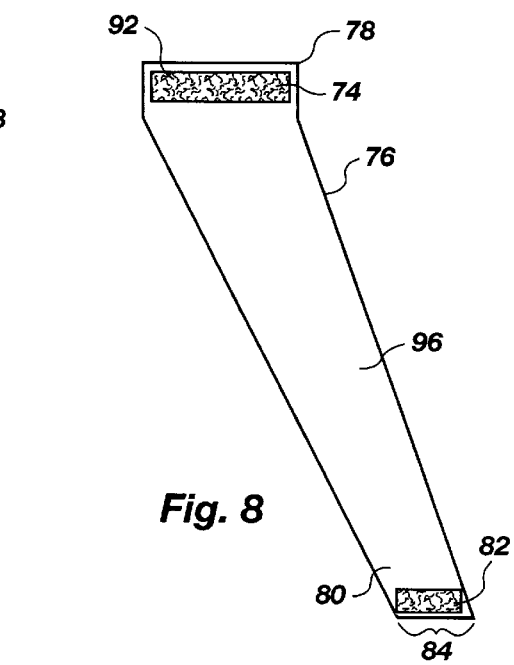
FIG. 8 is a plan view of the inner facing surface of the single bracing member shown in FIG. 7 with the inner facing surface being shown.

FIGS. 7 and 8 illustrate the bracing member 76 which, like bracing member 36, comprises a length of material which has a longitudinal axis 86 formed through the length thereof. The bracing member 76 may preferably be constructed to have a greater width 90 at the proximal end 78 compared with the width 84 at the distal end 80 and, as such, may be considered to have a tapered configuration. The material from which the bracing member 76 is made may be any suitable material which provides a certain flexibility to permit winding the brace member 76 about the leg 30 in a circumferentially spiraling fashion as illustrated in FIG. 6. As described for bracing member 36, it is equally important for bracing member 76 to be substantially inelastic or non-extendible along the longitudinal axis 86 thereof. The material of the bracing member 76 may also be substantially inelastic in a direction 88 normal to the longitudinal axis 86 of the bracing member 76. However, some elasticity in direction 88 normal to the longitudinal axis 86 of the bracing member 76 may be beneficial in providing expandability to accommodate changes in muscle configuration as the muscles expand and contract with movement.

As shown in FIG. 8, the bracing member 76 may be constructed with a securement structure 92 on the inner surface 96 (i.e., that surface which is positioned toward the wearer's body) of the proximal end 78 for releasable securement of the bracing member 76 to bracing member support 32 or double-width bracing member support 70. Such securement structure 92 may, for example, be a hook and loop tab 74 or other suitable device. Also, the inner surface 96 of the distal end 80 of the bracing member 76 may be constructed with a securement means, such as, for example, a hook and loop tab 82 which is interlockable with the hook and loop material 46 positioned on the surface 50 of the second bracing member support 42 (FIG. 1).

FIG. 9 shows a side view of a portion of a human leg 30 and the bracing members 36 and 76 winding in levo- and dextrorotatory fashion respectively down the leg 30. A further embodiment of the present invention may include a plurality of material loops 98 attached to the flexible undersleeve 66 and positioned on both the medial (i.e., inside) and lateral (i.e., outside) sides of the knee joint 22 for the purpose of guiding the bracing members 36 and 76 in the proper positioning about the leg to facilitate active resistance to axial rotation about the knee joint 22. The material loops 98 may have a degree of elasticity such that they do not significantly alter the flexibility of either the bracing members 36 and 76 or the flexible undersleeve 66. This view also illustrates the preferred positioning of the bracing members 36 and 76 as they pass the knee joint 22. In a preferred embodiment of the present invention, the bracing members 36 and 76 pass along the medial and lateral condyles of the knee joint without passing directly over the patellar region or the area directly posterior to the knee joint 22. The flexible undersleeve may be provided with a patellar relief cut-out 68 in those instances where this relief is considered advantageous.

FIG. 10 illustrates one exemplar means of attaching the distal ends 44 and 80 of both the levo-and dextrorotatory-winding bracing members, 36 and 76, respectively, to the second bracing member support 42. The distal end 44 of each levorotatory-winding bracing member 36 may pass behind the second bracing member support 42 (i.e. between the second bracing member support 42 and the leg 30) and is inverted back over the second bracing member support 42 to engage a suitable securement means, shown here as the corresponding hook and loop material 46 of the second bracing member support 42 with tab 48 (shown in phantom) of the bracing member 36. Alternatively, where the flexible undersleeve is utilized, the distal end 44 of bracing member 36 would pass between the second bracing member support 42 and the flexible undersleeve 66 and is inverted back over the second bracing member support 42 to engage the corresponding hook and loop material 46 with tab 48. The dextrorotatory-winding bracing members 76 are shown attached directly to the hook and loop material 46 of the second bracing member support 42 through hook and loop tabs 82 (shown in phantom).

Alternatively from the arrangement shown in FIG. 10, the levorotatory bracing members 36 could attach directly to the outer surface 50 of the second bracing member support 42 and the dextrorotatory-winding bracing members 76 may pass behind the second bracing member support 42 (i.e., between the second bracing member support 42 and the leg 30) and be inverted back over the second bracing member support 42 to engage the corresponding hook and loop material 46 with tab 82 which, in this embodiment, would be positioned on the outer facing surface of the bracing member 76. Again, where the flexible undersleeve is utilized, the distal end 80 of bracing member 76 would pass between the second bracing member support 42 and the flexible undersleeve 66 and inverted back over the second bracing member support 42 to engage the corresponding hook and loop material 46 with tab 82 of the bracing members 76. The means of attaching the bracing members 36, 76 to the first bracing member support 32 or 70 and the second bracing member support 42 are by way of example only and many other suitable securement means may be employed.

FIGS. 11(a), 11(b), 12(a) and 12(b), illustrate an alternative embodiment of a bracing member, showing a dextrorotatory example (FIG. 1) and a levorotatory example (FIG. 12). A dextrorotatory bracing member 100 (FIGS. 11(a) and 11(b)) of this embodiment comprises a combination of two bracing members 76 previously described. FIG. 11(a) shows the outer facing surface 120 (i.e. facing away from the body) of bracing member 100 and FIG. 11(b) shows the inner facing surface 121 of bracing member 100. Bracing member 100 consists of one complete bracing member 76 and the proximal half 76' of a second bracing member attached thereto as illustrated. The material from which bracing member 100 is constructed has characteristics equivalent to those described for bracing members 36 and 76. That is, the material has a certain flexibility to allow for winding of the bracing member around the leg in a circumferentially spiraling fashion. As for bracing members 36 and 76, it is important in the delimiting of axial rotation about the knee joint 22 that each section 76 and 76' of bracing member 100 be substantially inelastic or non-extendible along the longitudinal axes 104, 104' thereof. The material of bracing member 100 may also be substantially inelastic in a direction 112, 112' normal to the longitudinal axes 104, 104' of segments 76 and 76', respectively. However, some elasticity in direction 112, 112' of the segments 76 and 76' may be beneficial in providing expandability of the bracing member 100 to accommodate changes in muscle configuration as the muscles contract and expand during activity.

Bracing member 100 may be constructed to have a greater width 106, 106' at the proximal ends 102, 102' compared to the width 108 at the distal end 110. As such, the bracing member 100 may be considered to have a tapered configuration. Bracing member 100 may also be constructed with a securement structure 114, 114' for releasable securement of proximal ends 102, 102' of bracing member segments 76 and 76' to first bracing member support 32 (or 70). The securement structure 114, 114' may, for example, be a hook and loop tab 116, 116' at the proximal ends 102, 102' of bracing member segments 76 and 76' of bracing member 100. The distal end 110 of bracing member 100 may also have a securement structure 118 for releasable securement of the distal end of bracing member 100 to bracing member support 42. This securement structure 118 may, for example, be a hook and loop tab 123 which releasably attaches to the corresponding hook and loop material 46 on bracing member support 42.

For a levorotatory bracing member, as shown in FIGS. 12(a) and 12(b), bracing member 101 comprises a combination of two bracing members 36 as previously described. FIG. 12(a) shows the outer facing surface 122 (i.e. facing away from the body) of bracing member 101 and FIG. 12(b) shows the inner facing surface 124 of bracing member 101. Bracing member 101 consists of one complete bracing member 36 and the proximal half 36' of a second bracing member attached thereto as illustrated. The material from which bracing member 101 is constructed has characteristics equivalent to those described for bracing members 36 and 76. That is, the material has a certain flexibility to allow for winding of the bracing member around the leg in a circumferentially spiraling fashion. As for bracing members 36 and 76, it is important in the delimiting of axial rotation about the knee joint 22 that each section 36 and 36' of bracing member 101 be substantially inelastic or non-extendible along the longitudinal axes 105, 105' thereof. The material of bracing member 101 may also be substantially inelastic in a direction 113, 113', normal to the longitudinal axes 105, 105' of segments 36 and 36'. However, some elasticity in direction 113, 113' of the segments 36 and 36' may be beneficial in providing expandability of the bracing member 101 to accommodate changes in muscle configuration as the muscles expand and contract during activity.

Bracing member 101 may be constructed to have a greater width 107, 107' at the proximal ends 103, 103' compared to the width 109 at the distal end 111. As such, the bracing member 101 may be considered to have a tapered configuration. Bracing member 101 may also be constructed with a securement structure 115, 115' for releasable securement of the proximal ends 103, 103' of bracing member segments 36 and 36' to the first bracing member support 32 (or 70). The securement structure 115, 115' may, for example, be a hook and loop tab 117, 117' at the proximal ends 103, 103' of bracing member segments 36 and 36' of bracing member 101. The distal end 111 of bracing member 101 may also have a securement structure 119 for releasable securement of the distal end 111 of bracing member 101 to bracing member support 42. This securement structure 119 may, for example, be a hook and loop tab 125 which attaches to the corresponding hook and loop material 46 on bracing member support 42.

Figure 13:
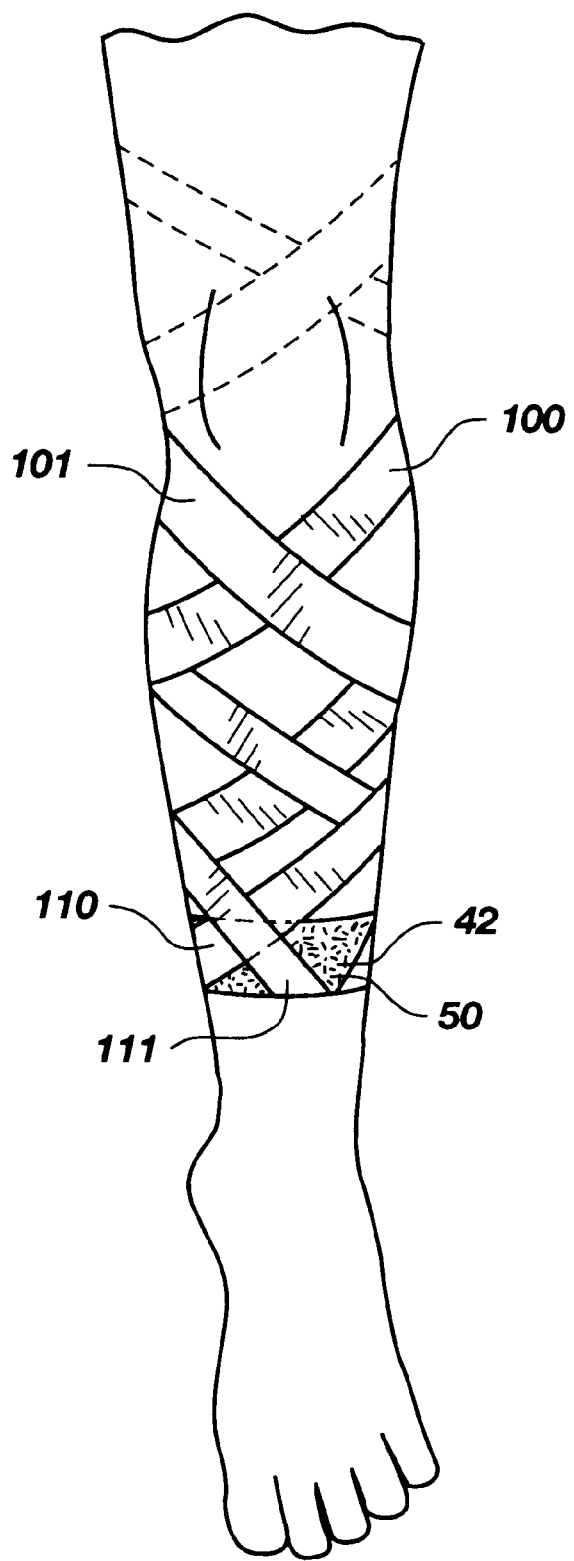
FIG. 13 is a front view of the lower portion of a leg illustrating the method of securement of the bracing members shown in FIG. 11(a) and FIG. 12(a) to the second bracing member support.

The advantage of the bracing members 100, 101 shown in FIGS. 11(a), 11(b), 12(a) and 12(b) is that it simplifies the securement of the bracing members 100 and 101 to the bracing member supports 32 (or 70) and 42, particularly at the second bracing member support 42. That is, rather than having eight distal ends (four distal ends 44 of bracing members 36 and four distal ends 80 of bracing members 76) to secure to the second bracing member support 42, as shown in FIG. 6, this embodiment results in having only two bracing members 100, 101 per direction to secure to the second bracing member support 42, or four distal ends 110, 111. FIG. 13 illustrates, for example, attachment of the four such distal ends 110, 111 of bracing members 100, 101 (although only one distal end 110, 111 of each bracing member 100, 101 is viewable in full) at their point of securement to the second bracing member support 42, approximately in anterior-posterior and medial-lateral positions. All four distal ends 110, 111 of the bracing members may be secured to the outer surface 50 of the second bracing member support 42.

Figure 14:
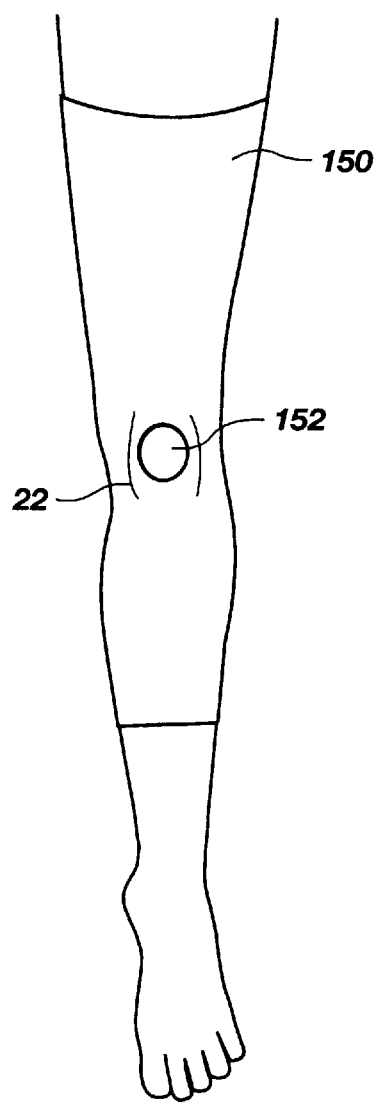
FIG. 14 is a front view of the leg illustrating an outer sleeve positionable over the wound bracing members.

FIG. 14 illustrates another alternative embodiment of the invention in which a second flexible sleeve 150 may be positionable over the entire bracing apparatus (e.g., shown in FIG. 6). The flexible sleeve 150 is sized in length to extend from a distance above the knee joint 22 to a distance below the knee joint 22, enclosing all components described thus far, and may extend from the top of bracing member support 32 (FIG. 1) to the bottom of bracing member support 42 (FIG. 1). The flexible sleeve 150 may also have a patellar relief space 152 positioned directly over the patellar region of knee joint 22.

Figure 15:
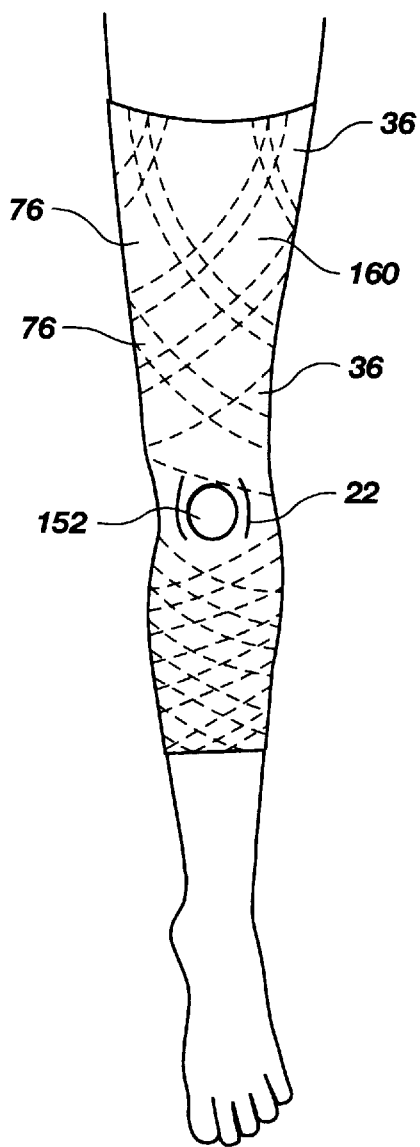
FIG. 15 is a view in elevation of an alternative embodiment of the invention where the bracing members are integrally formed in a sleeve member.

The embodiments of the present invention described previously generally comprise circumferentially spiraling bracing members which are attached to first and second bracing member supports. However, in an alternative embodiment, the bracing members and bracing member supports may be integrally formed as part of an oversleeve 160 which is positionable on the wearer's body about the target joint, as shown in FIG. 15. The oversleeve 160 preferably extends a distance from one side of the joint to the other side of the joint and may look much like the oversleeve 150 illustrated in FIG. 14. In this embodiment, spiraling lengths of material which form the bracing members 36 and 76 may be associated with a surface (e.g., the inner surface) of the oversleeve 160, such as by enclosing each spiraling length of material in a pocket or casing. Alternatively, the oversleeve 160 may be constructed with inelastic lengths of thread, ribbons or material which provides the same circumferential spiraling and actively resistant force provided by individually wound bracing members as previously described.

The degree of resistance to axial rotation about a joint (e.g., the knee) in the present invention is dependent upon the degree to which the individual bracing members are adjustably tightened about the joint, relative to the normal unstressed position of that joint. Application of the bracing members to the bracing member supports while the limb is in a normal, frontal position will result in a sufficient degree of spiraling compression about the limb to provide for active resistance to axial rotation. However, the desired degree of resistance to axial rotation in the joint may be both activity-dependent and a function of personal preference. It may therefore be desirable to provide for optionally increasing the spiraling compression factor, and thus, the degree of active resistance to rotation, by further adjustment of the bracing members in one or both directions of rotation (internal and/or external). This involves selectively adjusting the tightness of the bracing members 36 and 76 (or 100 and 101) about the limb (e.g., the leg) in either or both the levorotatory and/or dextrorotatory directions. The tightening of the bracing apparatus will be described for adjustment of the bracing members on a left leg and for resistance to internal tibial rotation about the knee joint.

The bracing apparatus 20 is first placed on the leg as previously described by securing the proximal ends of a first set of bracing members (e.g., 36) to the first bracing member support (e.g. 70) and sequentially winding each bracing member 36 about the leg in a spiraling fashion until the distal ends 44 are secured to the second bracing member support 42. Then the proximal ends of a second set of bracing members (e.g., 76) are attached to the first bracing member support (e.g. 70) and are sequentially wound in a spiraling fashion about the leg until the distal ends 80 of the bracing members 76 are secured to the second bracing member support 42.

From a normal or unstressed position (i.e., no angular rotation about the joint), the user adjusts the distal ends 80 of bracing members 76 attached to the second bracing member support 42 by pulling them in a downward direction until they are pulled to their fullest extent and then attaches each distal end 80 to the hook and loop material 46 located on second bracing member support 42. The user then rotates his body to the desired extent in an internal direction. For a brace on the left leg, this would be a rotation of the body (and the upper portion of the leg) to the right. The user then sequentially detaches the proximal end 78 of each bracing member 76, pulls the bracing member 76 in the direction opposite to that which defined the body turn (i.e., to the left) to a selected degree to impose a tautness along the longitudinal axis 86 of the bracing member 76 and reattaches the proximal end 78 of each bracing member 76 to the first bracing member support 70 by means of, for example, the hook and loop material 74. Increasing resistance to axial rotation in the opposite direction would involve an analogous procedure using the bracing members 36 winding in a direction opposite to bracing members 76. If bracing members 36 lie beneath bracing members 76 as shown in FIG. 6, the proximal ends 78 of bracing members 76 may be temporarily detached to access the proximal ends 38 of bracing members 36 for adjustment.

When the user returns to the normal, frontal orientation, the distance between the point of attachment of the distal end 80 of a bracing member 76 and the point of attachment of the proximal end 78 of the bracing member 76 is increased relative to that distance described between those points when the leg was rotated. This results in the bracing system 20 exerting a degree of pre-load compression when in a normal, frontal orientation. The brace will then exert additional compressive and restraining force against axial rotation as the angle of rotation about the joint increases because the circumference of the bracing member 76, defined by the spirally-winding configuration thereof, decreases, providing increased compression and thereby limiting axial rotation. Notably, either set of bracing members 36 or 76, or both, may be selectively adjusted. It should also be noted that the dextrorotary-winding bracing members may be attached closest to the leg with the levorotary-winding bracing members being positioned thereover, or vice versa. In a unitary or integrally formed embodiment of the brace, the flexible member may be constructed to provide adjustable, pre-loaded resistance to rotation through circumferentially spiraling resistance.

Figure 16:
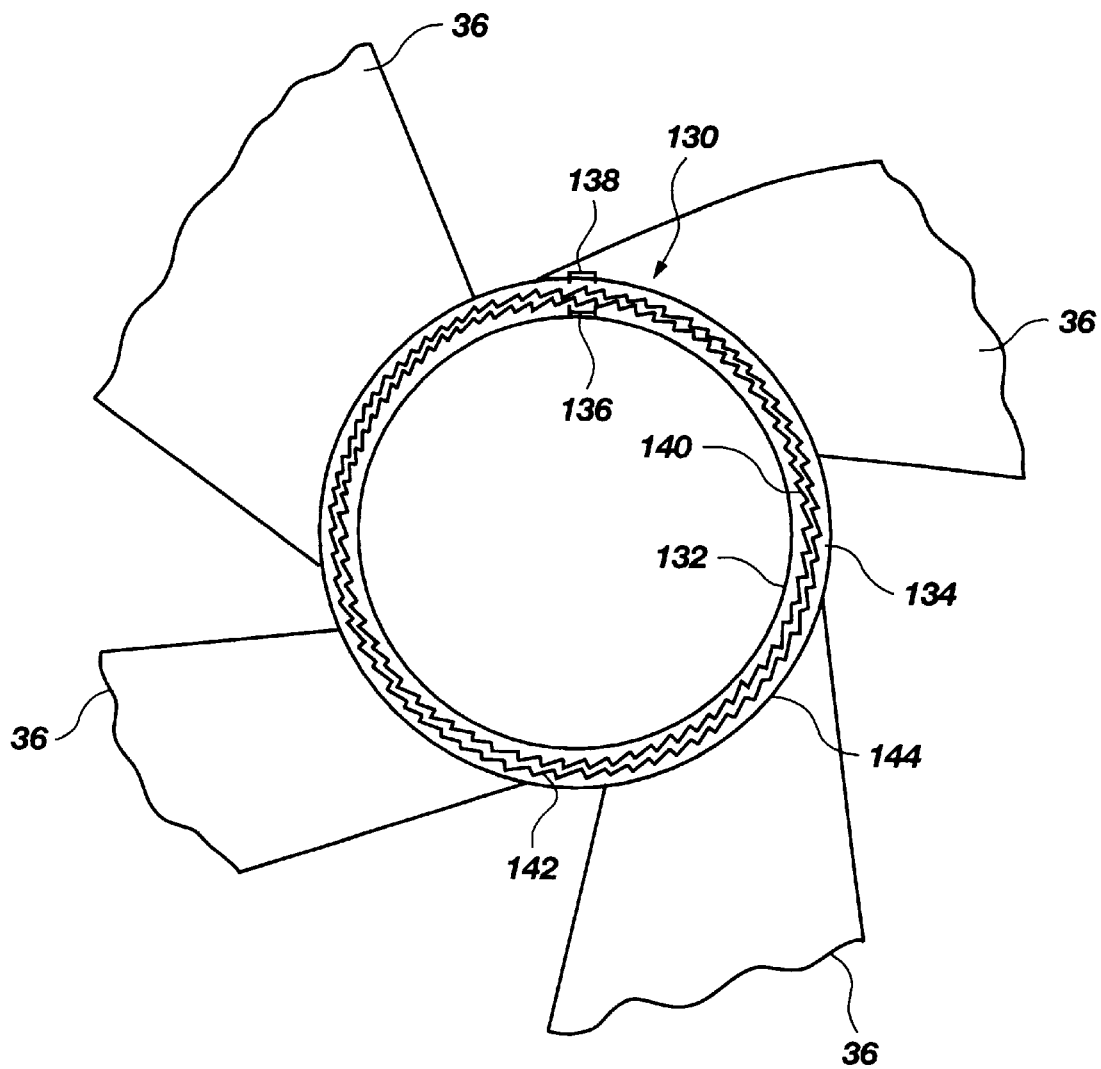
FIG. 16 is a plan view of an alternative embodiment of the bracing member support having a ratcheting system for providing adjustability of the bracing members.

FIG. 16 illustrates an alternative embodiment providing simplified adjustability of the bracing members relative to a bracing member support by providing an articulating bracing member support 130 which may be structured with a ratchet-like gearing mechanism. As illustrated, the bracing member support 130 may comprise an inner band 132 sized to encircle the wearer's leg and an outer band 134 sized to encircle the inner band 132. The outer band 134 provides attachment of the bracing members, here shown as bracing members 36, to the outer surface 144 thereof. The inner band 132 may be constructed with a locking expansion clip 136, which joins free ends of the inner band 132, to allow the inner band 132 to be expanded in circumference to facilitate applying the bracing member support 130 to the limb and to uniquely accommodate the circumference of the wearer's leg. The outer band 134 may also have a locking expansion clip 138 which allows the outer band 134 to be positioned over and secured in registration against the inner band 132 as shown. The inner band 132 and outer band 134 may be constructed of a relatively rigid material such as a hard plastic, or the inner band 132 and outer band 134 may be structured from a pliant or more flexible material which facilitates comfort in the wearing of the brace. The articulating bracing member support 130 may be a separate structure secured to leg 30 or, alternatively, may be constructed to be an integral part of an undersleeve 66 positioned against the wearer's body.

The inner band 132 is structured with tooth-like projections 140 which interlock with tooth-like projections 142 positioned on the outer band 134 in a manner which brings the tooth-like projections 142 of the outer band 134 in locking registration against the tooth-like projections 140 of the inner band 132. With the locking expansion clip 138 in the locked position, the outer band 134 may be rotated relative to the inner band 132 so that the tooth-like projections 142 of the outer band 134, in a ratcheting manner, can slip past the tooth-like projections 140 of the inner band 132 in one direction only. The tooth-like projections 140, 142 interlock and prevent the outer band 134 from moving in the opposite direction relative to the inner band 132. This allows the bracing members (e.g. 36, 76) attached thereto to be adjustably tightened to the desired degree of compression while preventing them from returning to the position of original registration.

In use, the inner band 132 is positioned about the user's leg and is locked in place by securement of the locking expansion clip 136. The outer band 134, with attached bracing members 36 or 76, is then secured in place about the inner band 132 with corresponding tooth-like projections 140, 142 engaged. The locking expansion clip 138 of the outer band 134 may provide the means by which the outer band 134 may be locked into position over the inner band 132, as well as providing a means by which the outer band 134 may be disengaged from the inner band 132 to rotate freely thereabout.

Figure 17:
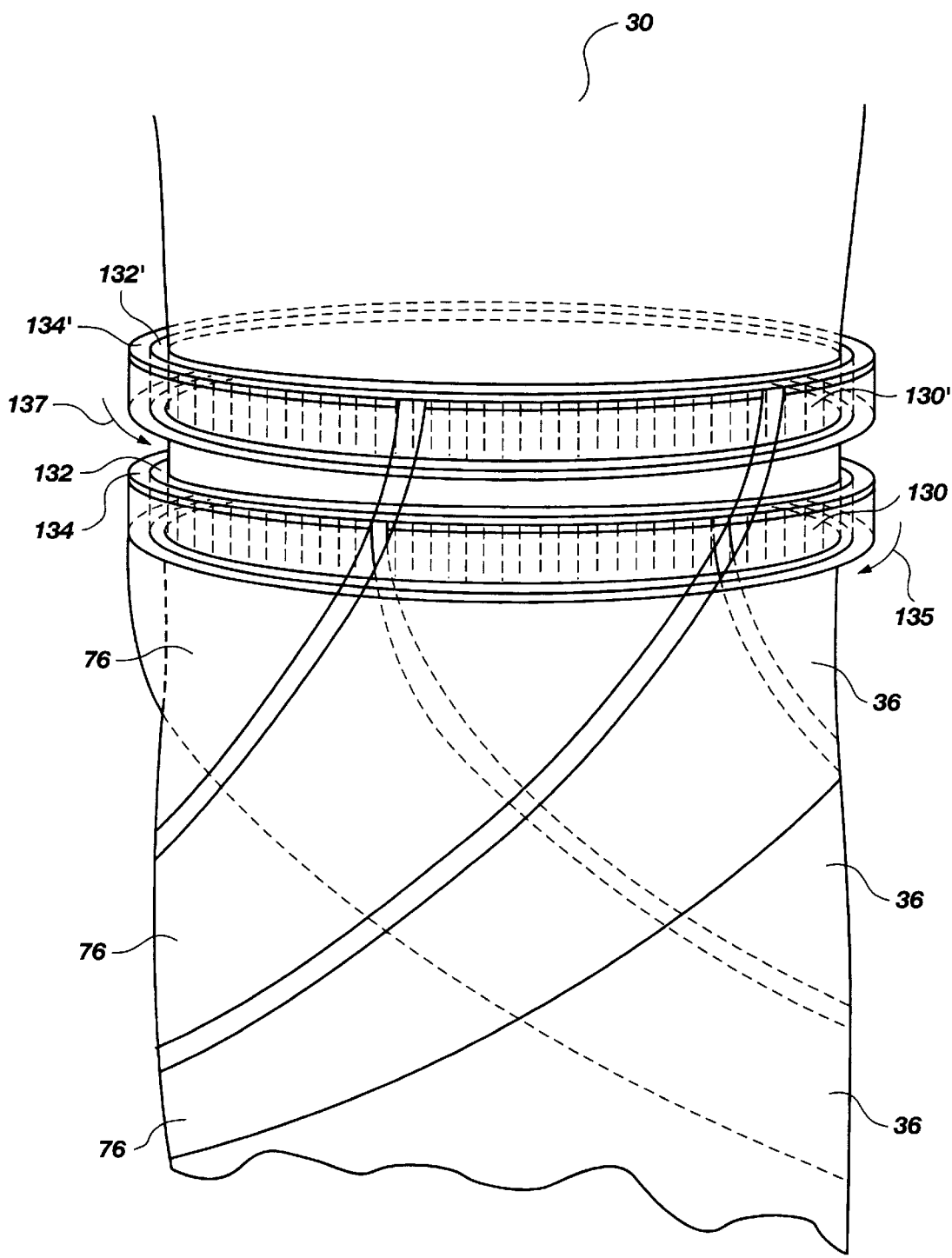
FIG. 17 is a front view of a portion of a leg illustrating the alternative embodiment of articulating bracing member supports shown in FIG. 16.

FIG. 17 shows a particularly suitable embodiment where two articulating bracing members 130 are employed, one to support the proximal ends of bracing members 36 and one to support bracing members 76. There may be a pair of articulating bracing member supports 130 located proximal to the knee joint. The point of attachment for the bracing members 36, 76 in the area distal to the knee joint may consist of a second bracing member support 42, as previously described, or may consist of two additional articulating bracing member supports 130 located distal to the knee joint. In FIG. 17, the bracing members 36, wound in a levorotatory direction, are attached to the lower articulating bracing member support 130, consisting of inner band 132 and outer band 134. The arrangement of the ratcheting teeth in this bracing member support 130 such that outer band 134 may rotate only in the direction of arrow 135 relative to the fixed inner band 132 (consistent with the direction in which the bracing members 36 are wound) thus tightening the levorotatory-wound bracing members 36 against the leg 30. The dextrorotatory-wound bands 76 may be attached to the upper articulating bracing member support 130' consisting of inner band 132' and outer band 134'. The arrangement of the ratcheting teeth in the upper articulating bracing member support 130' is such that outer band 134' may rotate only in the direction of arrow 137 with respect to the fixed inner band 132' (in a direction consistent with the dextrorotatory winding of the bracing members 76) again resulting in a tightening of those bracing members 76 against the leg 30.

The attachment of bracing members 36 and 76 (or 100 and 101 as shown in FIGS. 11(*a*) and 12(*a*)) may be reversed. That is, the levorotatory-wound bracing members may be attached to the upper articulating bracing member support 130' and the dextrorotatory-wound bracing members may be attached to the lower articulating bracing member support 130. This mode of attachment of the proximal portions of bracing members 36 and 76 (or 100 and 101) to the articulating bracing member supports 130 and 130' may also be applied to attachment of the distal ends 44, 80 of the bracing members 36 and 76 (or 100 and 101) to an equivalent set of articulating bracing member supports located on the distal side of the target joint.

The method for tightening the bracing members 36, 76 (or 100 or 101) using articulating bracing member supports such as 130, 130' is similar for both the internal and external directions and will be described with respect to the left leg and adding resistance to axial rotation in the direction of internal tibial rotation. From a normal, unstressed position (i.e., no angular rotation about the joint), the user rotates his body (as well as the upper portion of the leg) a selected degree in an inward direction. Again, if the brace is on the left leg, the user would rotate to the right. Rotation of the body causes the bracing members 76 (or 100) to slacken slightly along the longitudinal axis thereof so that the spirally-circumferential winding is loosened (i.e., lessened compressive force). With the locking expansion clip 138 closed, the outer band 134' of the upper bracing member support 130' is then grasped and rotated relative to the inner band 132' in a direction 137 opposite the direction of rotation of the body (i.e., to the left) until the bracing members 76 achieve the desired degree of tautness. As the user rotates the body and leg back to a normal (i.e., forward or non-rotated) position, an amount of pre-loaded compression is exerted in the bracing members 76 to actively resist axial rotation in the joint. Further rotation about the joint will result in increased resistance to axial rotation about the joint. The same tightening procedure may be followed with the bracing members 36 wound in the opposite (i.e., levorotatory) direction by rotating the body outwardly, or to the left, and rotating the outer band 134 of the lower bracing member support 130 relative to the inner band 132 in direction 135.

Analytical

Analytical data was obtained using an anatomically correct, instrumented knee surrogate model in which the principal ligaments of the knee are individually represented by cables, which were attached to strain gauges. The strain gauges were monitored by computer in order to determine the loads on the individual "ligaments" when an external torque of known quantity was applied in a direction perpendicular to the longitudinal axis of the femur (i.e., a rotational torque was applied about the knee joint) while the tibia was fixed in place. The applied torque thus resulted in a rotation of the femur relative to the tibia. In addition, the angle of rotation through which the femur moved relative to the tibia was also measured. Data relating to an unbraced leg and data relating to a leg fitted with the brace of the present invention were collected and compared.

Figure 18:
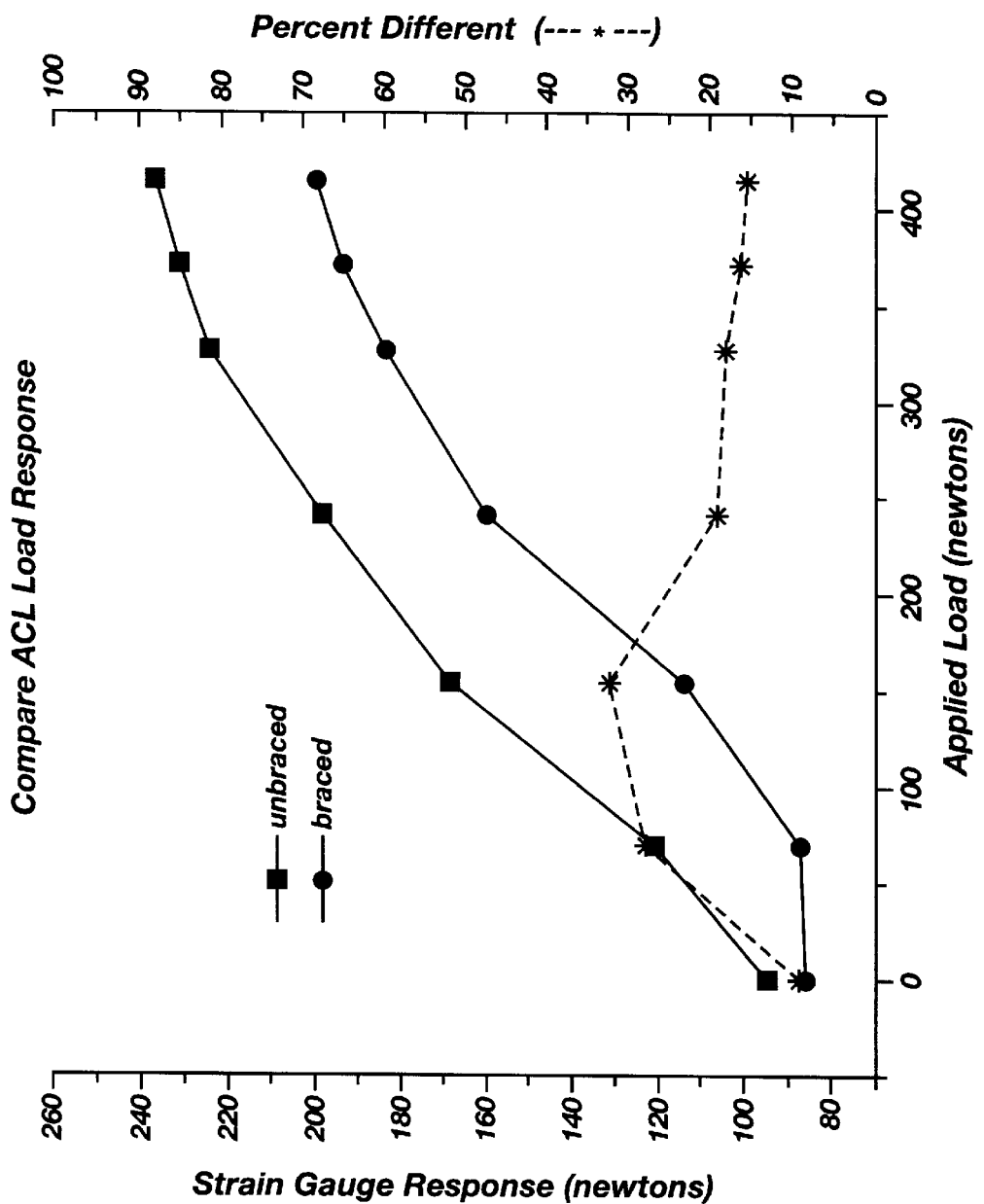
FIG. 18 is a graph illustrating the increased resistance to ACL load provided by the present invention relative to an unbraced leg.
Figure 19:
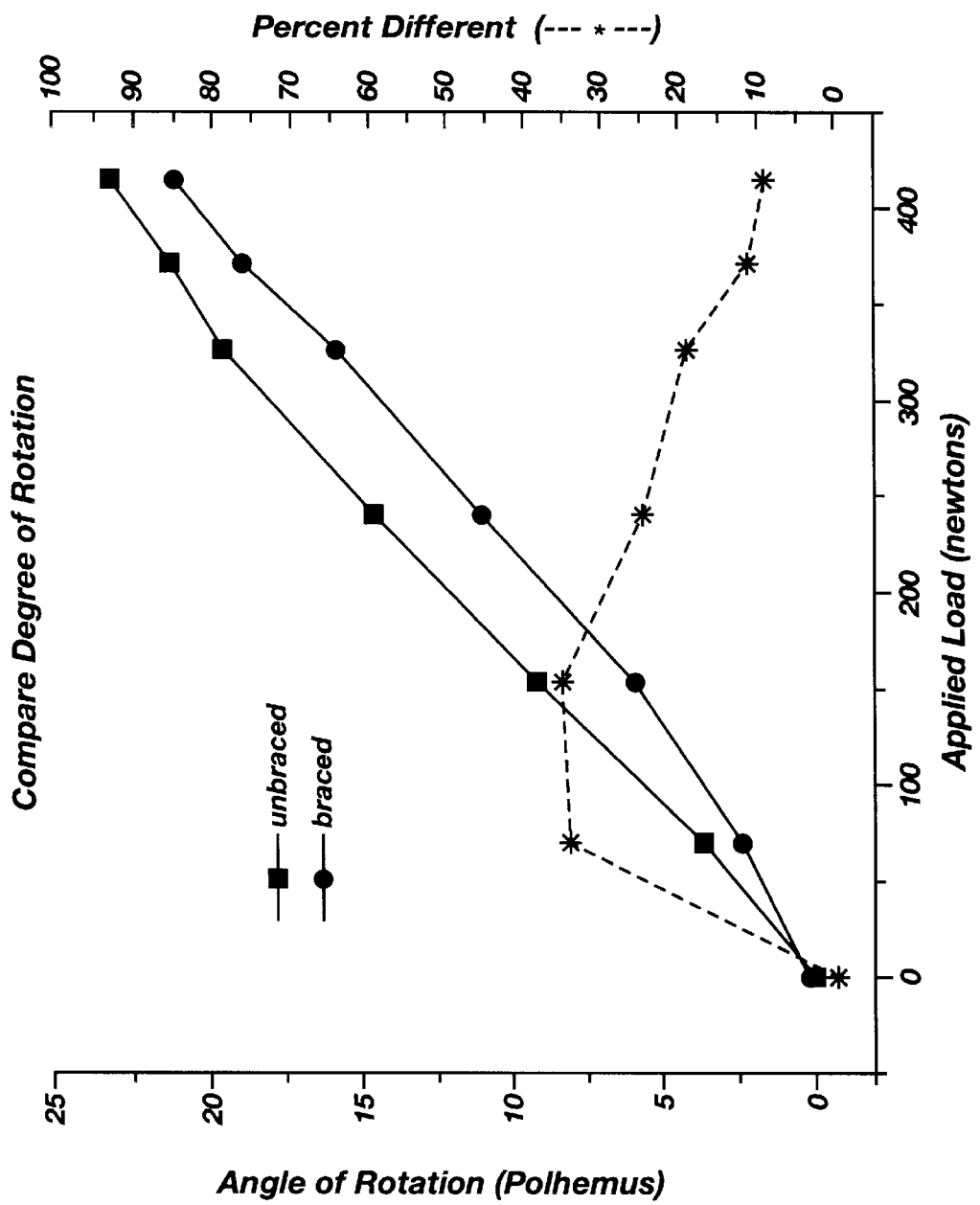
FIG. 19 is a graph illustrating the increased resistance to rotation provided by the present invention as compared to an unbraced leg.

FIG. 18 illustrates representative data for the anterior cruciate ligament (ACL) strain gauge over a range of applied torque from 70 to 413 Newton (12 to 70 Nm). The data show a consistent decrease in load on the ACL in the braced condition compared to the unbraced condition. The average decrease in load on the ACL in the braced versus unbraced condition was approximately 25 % under these experimental conditions. FIG. 19 illustrates representative data for the degree of rotation of the femur relative to the tibia over the same range of applied load in a braced leg. These data show a consistent decrease in the degree of rotation of the femur relative to the tibia over the range of applied load. The percent reduction in rotation under the experimental conditions used was approximately 25%.

Figure 20:
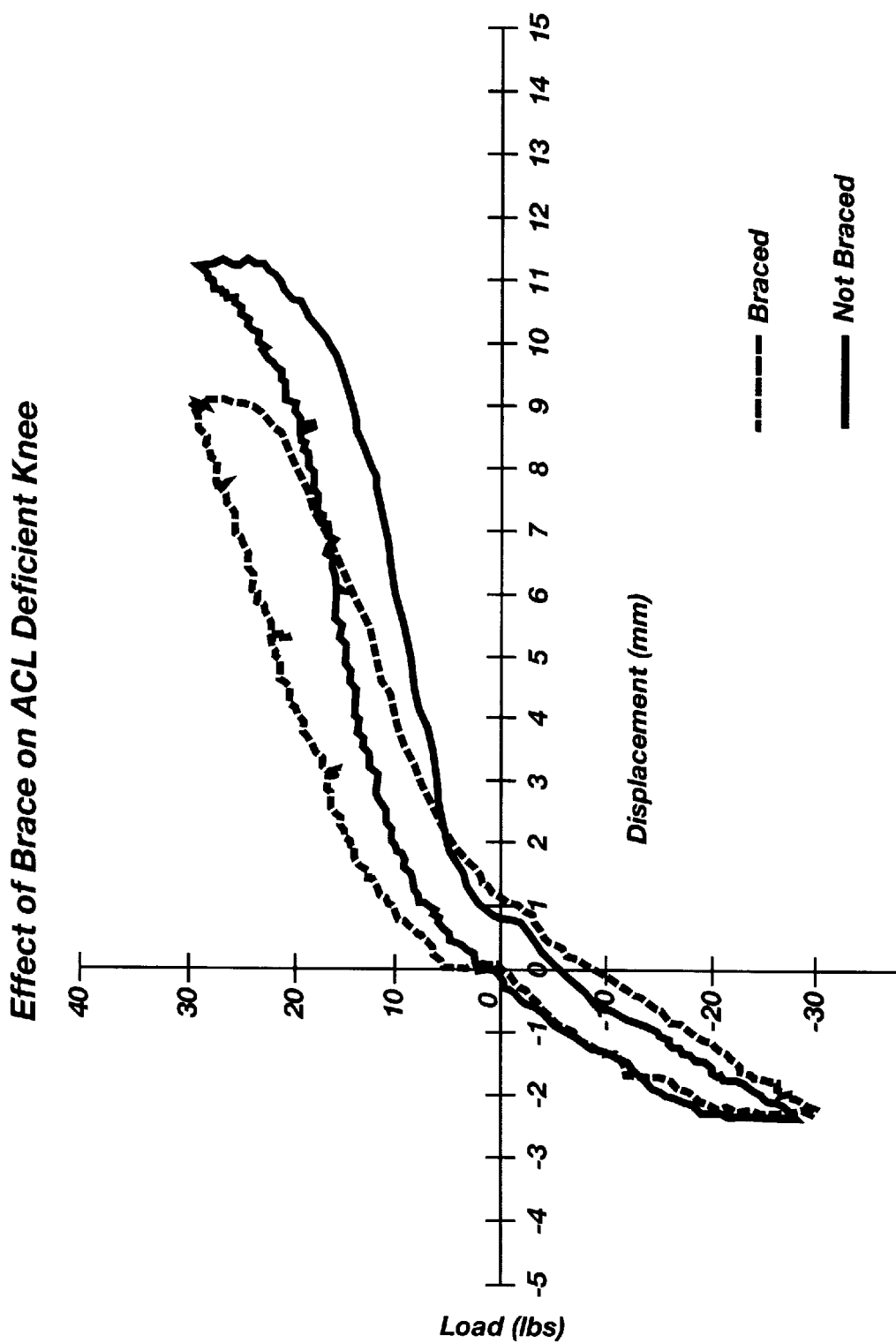
FIG. 20 is a graph illustrating the effectiveness of the present invention in facilitating resistance to anterior tibial displacement in ACL-deficient knees, as compared with an unbraced leg.

Additional data was obtained to determine the effect of the brace on decreasing anterior tibial translation in the knee joint using a KT-2000 Arthrometer (Medtronic Corp., San Diego, Calif.). FIG. 20 illustrates representative data in which the subject was an ACL-deficient male, showing the effect of the brace on translation in the knee joint. The data clearly indicate a clinically significant reduction in anterior tibial translation in the braced condition relative to the unbraced condition. Specifically, these data show that more applied force is required to initiate translation in the braced condition (~6 lb.) compared to the unbraced condition (~3 lb.), that at a given applied force, for example 15 lb., translation is greater in the unbraced condition (~6 mm) compared to the braced condition (~2 mm) and that at the maximum applied force of about 30 pounds, there is a difference of over 2 mm less translation in the braced condition compared to the unbraced condition. These data demonstrate the effectiveness of the present invention in decreasing load on the ACL, decreasing rotation about the knee joint, and decreasing anterior tibial translation.

The present invention represents a new concept in orthopedic bracing, the primary function of which is to offer active resistance to axial rotation about the joint. The device represents a significant departure from the historical use of rigid structures which complicate the fitting of the brace to an individual leg. There is no mechanical hinge in the present invention and thus no need for careful measurement of condyle distances and the elaborate use of foam or inflatable pads to enhance the comfort of the brace. The present invention can be fabricated from a lightweight flexible material which provides a more comfortable bracing system and one which more effectively addresses the concerns related to excessive axial rotation and translation about a joint. While the present invention may be used as a stand alone bracing system, it may also provide additional benefit when used in combination with current post-hinge-strap bracing technology. While the illustrated embodiment of this invention demonstrates its applicability to the knee joint, the brace may be applied to any joint in connection with which axial rotation is to be resisted in any degree, and can be used in both humans and animals alike. The illustrated embodiments of the present invention are intended to be merely exemplary and those skilled in the art will understand that numerous variations and modifications of the illustrated embodiments may be made without departing from the present invention as defined by the claims. All such variations are intended to be within the scope of the present invention as defined in the claims.

What is claimed is:

1. An orthopedic brace providing active resistance to axial rotation and translation in a joint comprising an attachment member, at least one circumferentially spiraling bracing member having a proximal end for positioning on one side of a joint and attached to said attachment member and a terminal distal end for positioning on the other side of the joint along a longitudinal axis formed through the joint and attached to said attachment member at least one of said proximal end or said terminal distal end being detachably attached to said attachment member, and a continuous circumferentially spiraling distance of singular direction extending between said proximal end and said distal end defining a circumference orientated about the joint from said proximal end to said distal end, active resistance to axial rotation and translation of the joint being provided by a change in said circumference responsive to a change in position of said proximal end relative to said distal end, said at least one circumferentially spiraling bracing member sized to provide body-compressive force about a joint proximal and distal to the joint.

2. The orthopedic brace of claim 1 wherein said at least one circumferentially spiraling bracing member further comprises at least one bracing member which circumferentially spirals about the joint in a levorotatory direction and at least one circumferentially spiraling bracing member which circumferentially spirals about the joint in a dextrorotatory direction.

3. The orthopedic brace of claim 1 further comprising a first bracing member support for positioning on one side of the joint and a second bracing member support for positioning on the other side of the joint along a longitudinal axis formed through the joint, said at least one circumferentially spiraling bracing member being attached to said first bracing member support and said second bracing member support by attachment of said proximal end and said distal end to one of each said first bracing member support and said second bracing member support.

4. The orthopedic brace of claim 3 wherein said proximal end of said at least one circumferentially spiraling bracing member is detachably attached to said first bracing member support to render said at least one circumferentially spiraling bracing member adjustable along said circumferentially spiraling distance to modify said circumference and selectively adjust the active resistance to axial rotation and translation in the joint.

5. An orthopedic brace for actively resisting axial rotation and translation in a joint comprising:
   a first bracing member support for positioning on one side of a joint;
   a second bracing member support for positioning on the other side of the joint and spaced from said first bracing member along a longitudinal axis formed through the joint;
   at least one circumferentially spiraling bracing member having a first terminal end attached to said first bracing member support and a second terminal end attached to said second bracing member support, said attached first end and said attached second end defining a distance therebetween along a unidirectional circumferentially spiraling line which encircles the joint to define a circumference thereabout, said circumference being selectively adjustable to resist axial rotation and translation in the joint, said at least one circumferentially spiraling bracing member being sized to provide a compressive force against the body about the joint proximal and distal to the joint.

6. The orthopedic brace of claim 5 wherein the length of said distance of said circumferentially spiraling line is fixed while said circumference is selectively adjustable.

7. The orthopedic brace of claim 6 wherein said at least one circumferentially spiraling bracing member comprises at least one circumferentially spiraling bracing member wound in a levorotatory direction about the joint and at least one circumferentially spiraling bracing member wound in a dextrorotatory direction about the joint, said circumferentially spiraling bracing members being independently adjustable.

8. The orthopedic brace of claim 7 wherein said first bracing member support and said second bracing member support are each sized to retain a plurality of circumferentially spiraling bracing members in detachable attachment thereto.

9. The orthopedic brace of claim 8 wherein said first terminal end of said at least one circumferentially spiraling bracing member has a width dimension and said second terminal end has a width dimension, said width dimension of said first end being different from the width dimension of said second end.

10. The orthopedic brace of claim 8 wherein each said at least one circumferentially spiraling bracing member has two first ends, each said first end being detachably attached to said first bracing member support.

11. The orthopedic brace of claim 7 further comprising a flexible undersleeve to which said first bracing member support and said second bracing member support are formed.

12. The orthopedic brace of claim 11 wherein said flexible undersleeve has an inner surface oriented for positioning against the wearer's skin, said inner surface being formed with a coefficient of friction sufficient to reduce the amount of movement between the flexible undersleeve and the wearer's skin.

13. The orthopedic brace of claim 12 wherein said inner surface of said flexible undersleeve is treated with a rubberized material.

14. The orthopedic brace of claim 11 wherein said flexible undersleeve includes a patellar relief opening to accommodate protrusion of the wearer's patella therethrough.

15. The orthopedic brace of claim 11 wherein said flexible undersleeve further comprises flexible straps for guiding said circumferential spiraling bracing members in circumferential and spiral winding about a joint.

16. The orthopedic brace of claim 11 further comprising an oversleeve sized to be coextensive with said flexible undersleeve.

17. The orthopedic brace of claim 7 further comprising an oversleeve sized to extend from one side of a joint to the other side of the joint and to overlay said first bracing member support, said second bracing member support and said at least one circumferentially spiraling bracing member.

18. The orthopedic brace of claim 17 wherein said first bracing member support, said second bracing member support and said at least one circumferentially spiraling bracing member are integrally formed with said oversleeve, and said at least one circumferentially spiraling bracing member is selectively adjustable along said longitudinal axis to modify said circumference.

19. The orthopedic brace of claim 6 wherein said first bracing member support further comprises securement apparatus formed therewith for detachable attachment of said at least one circumferentially spiraling bracing member to said first bracing member support.

20. The orthopedic brace of claim 19 wherein said at least one circumferentially spiraling bracing member further comprises securement apparatus formed therewith for detachable attachment of said at least one circumferentially spiraling bracing member to said first bracing member support.

21. The orthopedic brace of claim 20 wherein said securement apparatus of said at least one circumferentially spiraling bracing member and said securement apparatus of said first bracing member support comprises interlockable hook and loop material.

22. The orthopedic brace of claim 19 wherein said second bracing member support further comprises securement apparatus formed therewith for detachable attachment of said at least one circumferentially spiraling bracing member to said second bracing member support.

23. The orthopedic brace of claim 22 wherein said at least one circumferentially spiraling bracing member further comprises securement apparatus formed to said first terminal end for detachable attachment of said first terminal end to said first bracing member support, and comprises securement apparatus formed to said second terminal end for detachable attachment of said second terminal end to said second bracing member support.

24. The orthopedic brace of claim 6 wherein said at least one circumferentially spiraling bracing member further comprises securement apparatus formed on said first terminal end thereof for detachable attachment of said at least one circumferentially spiraling bracing member to said first bracing member support.

25. The orthopedic brace of claim 24 wherein said at least one circumferentially spiraling bracing member further comprises securement apparatus formed on said second terminal end thereof for detachable attachment of said at least one circumferentially spiraling bracing member to said second bracing member support.

26. The orthopedic brace of claim 6 wherein said first bracing member support and said second bracing member support are circumferentially adjustable.

27. The orthopedic brace of claim 26 wherein said first bracing member support and said second bracing member support are elastically expandable to be circumferentially adjustable.

28. The orthopedic brace of claim 26 wherein said first bracing member support further comprises an adjustable strap sized in length to encircle a limb and provide circumferential adjustability to said first bracing member support.

29. The orthopedic brace of claim 28 wherein said second bracing member support further comprises an adjustable strap sized in length to encircle a limb and provide circumferential adjustability to said second bracing member support.

30. The orthopedic brace of claim 6 wherein said first bracing member support further comprises an inner band and an outer band in interlocking relation to said inner band to provide rotational adjustment of said outer band relative to said inner band in one direction, said outer band being structured to retain said at least one circumferentially spiraling bracing member thereto.

31. The orthopedic brace of claim 30 wherein said inner band and said outer band are expandably flexible.

32. The orthopedic brace of claim 30 wherein said inner band and said outer band are each structured with a locking expansion device to increase the circumference of said inner band and said outer band from a first circumference to a second larger circumference.

33. The orthopedic brace of claim 30 wherein said first bracing member support further comprises a second inner band and a second outer band in interlocking relationship with said second inner band to provide rotational adjustment of said second outer band relative to said second inner band in one direction and said second outer band being structured to retain at least one circumferentially spiraling bracing member, said interlocking second inner band and second outer band being positioned adjacent said interlocking inner band and outer band and being oriented to rotate relative to each other in a direction which is opposite to the direction of rotation of said outer band relative to said inner band.

34. The orthopedic brace of claim 33 wherein said second bracing member support further comprises an inner band and an outer band in interlocking relationship to said inner band to provide rotational adjustment of said outer band relative to said inner band in one direction, said outer band being structured to retain said second end of said at least one circumferentially spiraling bracing member.

35. A method of bracing a physiological joint to provide active resistance to rotation about and translation in the longitudinal axis of the joint comprising:

providing at least one elongated bracing member which is structured to exert compressional force and resistance to rotation about the longitudinal axis of the joint;

positioning said at least one elongated bracing member to circumferentially and spirally wind in a single direction about said joint from a first point located on one side of the joint to a second point located on the other side of the joint along a longitudinal axis through the joint to define a circumference about the joint; and providing active resistance to rotation about the joint and compressional force against the body proximal and distal to the joint responsive to selective adjustment of said circumference.

36. The method according to claim 35 further comprising selectively varying the amount of resistance to rotation by selectively modifying said circumference about said joint by selectively adjusting the position of a first end of said elongated bracing member relative to a second end of said at least one elongated bracing member along a circumferentially spiraling line extending therebetween.

37. The method according to claim 36 wherein said at least one elongated bracing member comprises a plurality of elongated bracing members, at least one elongated bracing member being wound about said joint in a levorotatory direction and at least one elongated bracing member being wound about said joint in a dextrorotatory direction, each said elongated bracing member being selectively and independently adjustable to modify said circumference to vary the active resistance to rotation and translation exerted on said joint.

38. An orthopedic brace for actively resisting axial rotation and translation in a joint comprising:

a first bracing member support for positioning on one side of a joint;

a second bracing member support for positioning on the other side of the joint and spaced from said first bracing member along a longitudinal axis formed through the joint;

a plurality of circumferentially spiraling bracing members wound in a levorotatory direction about the joint, each having a first end for attachment to said first bracing member support and each having a second end for attachment to said second bracing member support, each said first end and its corresponding said second end defining a distance therebetween along a circumferentially spiraling line which encircles the joint to define a circumference thereabout, said circumference being selectively adjustable to resist axial rotation and translation in the joint; and a plurality of circumferentially spiraling bracing members wound in a dextrorotatory direction about the joint, each having a first end for attachment to said first bracing member support and each having a second end for attachment to said second bracing member support, each said first end and its corresponding said second end defining a distance therebetween along a circumferentially spiraling line which encircles the joint to define a circumference thereabout, said circumference being selectively adjustable to resist axial rotation and translation in the joint.

* * * * *